US 12,161,845 B2

(12) United States Patent
Scheurer et al.

(10) Patent No.: US 12,161,845 B2
(45) Date of Patent: Dec. 10, 2024

(54) ALTERNATIVE DEVICE FOR ADJUSTING A DOSAGE WITH A LIMITING MECHANISM FOR A DEVICE FOR ADMINISTERING A PRODUCT

(71) Applicant: Ypsomed AG, Burgdorf (CH)

(72) Inventors: Simon Scheurer, Bern (CH); Jürg Hirschel, Bern (CH); Andres Mellenberger, Koppigen (CH); Christian Schrul, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 899 days.

(21) Appl. No.: 17/160,764

(22) Filed: Jan. 28, 2021

(65) Prior Publication Data

US 2021/0146059 A1   May 20, 2021

Related U.S. Application Data

(63) Continuation of application No. PCT/IB2019/055547, filed on Jul. 1, 2019.

(30) Foreign Application Priority Data

Jul. 30, 2018   (EP) .................... 18186335

(51) Int. Cl.
  *A61M 5/31*   (2006.01)
  *A61M 5/24*   (2006.01)
  *A61M 5/315*   (2006.01)

(52) U.S. Cl.
  CPC .......... *A61M 5/31551* (2013.01); *A61M 5/24* (2013.01); *A61M 5/31541* (2013.01);
  (Continued)

(58) Field of Classification Search
  CPC .......... A61M 5/31533; A61M 5/31553; A61M 5/31551
  See application file for complete search history.

(56) References Cited

U.S. PATENT DOCUMENTS 2,771,217 A   11/1956   Brown et al.
2,991,662 A   7/1961   Johannes
(Continued)

FOREIGN PATENT DOCUMENTS

CH   617857 A5   6/1980
CH   703993 A2   3/2012
(Continued)

OTHER PUBLICATIONS

U.S. Appl. No. 12/403,849, USPTO Non-Final Office Action dated Sep. 28, 2009, 21 pages.
(Continued)

*Primary Examiner* — Nathan R Price
*Assistant Examiner* — Haden Matthew Ritchie
(74) *Attorney, Agent, or Firm* — Dorsey & Whitney LLP

(57) ABSTRACT

Dosing device for an administration device with a limiting mechanism containing: a dosing sleeve with a first stop and a stop wheel with a second stop means adapted to continually and proportionally follow a movement of the dosing sleeve during dosing movements. During an ejection movement, there is no relative movement between dosing sleeve and stop wheel. The first stop and the second stop each describe a path curve by their movements such that the two path curves intersect in one point and the stops contact one another and tilt the stop wheel, thereby blocking the dosing movement of the dosing sleeve. The stop wheel comprises first and third sloped surfaces that may form first and second gear guidances with a clutch thereby returning the stop wheel to a non-tilted position during up or down dosing movements when the stops do not contact another.

18 Claims, 27 Drawing Sheets

Fig. 1

(52) U.S. Cl.
CPC ...... *A61M 5/31558* (2013.01); *A61M 5/3156* (2013.01); *A61M 5/31563* (2013.01)

(56) References Cited

U.S. PATENT DOCUMENTS

| | | | |
|---|---|---|---|
| 3,082,914 | A | 3/1963 | Wilbur |
| 3,202,151 | A | 8/1965 | Kath |
| 3,411,366 | A | 11/1968 | Alfonso |
| 4,583,978 | A | 4/1986 | Porat et al. |
| 5,049,125 | A | 9/1991 | Accaries et al. |
| 5,263,475 | A | 11/1993 | Altermatt et al. |
| 5,514,097 | A | 5/1996 | Knauer |
| 5,569,236 | A | 10/1996 | Kriesel |
| 6,004,297 | A | 12/1999 | Steenfeldt-Jensen et al. |
| 6,123,684 | A | 9/2000 | Deboer et al. |
| 6,221,053 | B1 | 4/2001 | Walters et al. |
| 6,277,099 | B1 | 8/2001 | Strowe et al. |
| 6,582,404 | B1 | 6/2003 | Klitgaard et al. |
| 7,083,596 | B2 | 8/2006 | Saied |
| 7,112,187 | B2 | 9/2006 | Karlsson |
| 7,195,616 | B2 | 3/2007 | Diller et al. |
| 7,645,265 | B2 | 1/2010 | Stamp |
| 7,811,263 | B2 | 10/2010 | Burren et al. |
| 8,834,431 | B2 | 9/2014 | Kohlbrenner et al. |
| 9,114,211 | B2 | 8/2015 | Moeller et al. |
| 9,750,887 | B2 | 9/2017 | Hirschel et al. |
| 10,300,211 | B2 | 5/2019 | Kohlbrenner et al. |
| 10,350,363 | B2 | 7/2019 | Kohlbrenner et al. |
| 2004/0127858 | A1 | 7/2004 | Bendek et al. |
| 2004/0260247 | A1 | 12/2004 | Veasey et al. |
| 2005/0022806 | A1 | 2/2005 | Beaumont et al. |
| 2005/0065477 | A1 | 3/2005 | Jost |
| 2005/0080377 | A1 | 4/2005 | Sadowski et al. |
| 2005/0197626 | A1 | 9/2005 | Moberg et al. |
| 2005/0209570 | A1 | 9/2005 | Moller |
| 2005/0261634 | A1 | 11/2005 | Karlsson |
| 2006/0153693 | A1 | 7/2006 | Fiechter et al. |
| 2006/0184117 | A1 | 8/2006 | Knight et al. |
| 2006/0206057 | A1 | 9/2006 | Deruntz et al. |
| 2006/0264839 | A1 | 11/2006 | Veasey et al. |
| 2007/0016143 | A1 | 1/2007 | Miller et al. |
| 2007/0021715 | A1 | 1/2007 | Kohlbrenner et al. |
| 2007/0027430 | A1 | 2/2007 | Hommann |
| 2007/0225657 | A1 | 9/2007 | Hommann |
| 2008/0033369 | A1 | 2/2008 | Kohlbrenner et al. |
| 2008/0051712 | A1 | 2/2008 | Fiechter et al. |
| 2008/0051713 | A1 | 2/2008 | Kohlbrenner et al. |
| 2008/0171997 | A1 | 7/2008 | Kohlbrenner et al. |
| 2008/0234633 | A1 | 9/2008 | Nielsen |
| 2008/0287883 | A1* | 11/2008 | Radmer ............ A61M 5/3155 604/211 |
| 2008/0306445 | A1 | 12/2008 | Burren et al. |
| 2009/0048561 | A1 | 2/2009 | Burren et al. |
| 2009/0247959 | A1 | 10/2009 | Kohlbrenner et al. |
| 2009/0247960 | A1 | 10/2009 | Kohlbrenner et al. |
| 2009/0254035 | A1 | 10/2009 | Kohlbrenner et al. |
| 2009/0254044 | A1 | 10/2009 | Kohlbrenner et al. |
| 2009/0275916 | A1 | 11/2009 | Harms et al. |
| 2009/0299297 | A1 | 12/2009 | Moeller et al. |
| 2012/0283647 | A1 | 11/2012 | Cronenberg et al. |
| 2014/0350484 | A1 | 11/2014 | Kohlbrenner et al. |
| 2015/0073355 | A1* | 3/2015 | Hirschel ............ A61M 5/3156 604/207 |
| 2017/0035973 | A1 | 2/2017 | Schenker et al. |
| 2017/0043098 | A1 | 2/2017 | Kohlbrenner et al. |
| 2017/0361024 | A1 | 12/2017 | Hirschel et al. |
| 2019/0022332 | A1 | 1/2019 | Kohlbrenner et al. |
| 2019/0247587 | A1 | 8/2019 | Kohlbrenner et al. |
| 2019/0321558 | A1 | 10/2019 | Hirschel et al. |
| 2020/0306454 | A1 | 10/2020 | Hirschel et al. |

FOREIGN PATENT DOCUMENTS

| | | |
|---|---|---|
| CH | 706567 A2 | 11/2013 |
| DE | 20112501.3 U1 | 12/2002 |
| DE | 10229122 A1 | 2/2004 |
| DE | 102004063644 A1 | 7/2006 |
| DE | 102004063647 A1 | 7/2006 |
| EP | 0554995 A1 | 8/1993 |
| EP | 0554996 A1 | 8/1993 |
| EP | 0554996 B1 | 10/1996 |
| EP | 1681070 B1 | 2/2009 |
| EP | 1516638 B1 | 1/2010 |
| EP | 2814547 A1 | 12/2014 |
| EP | 2918298 A1 | 9/2015 |
| EP | 3603703 A1 | 2/2020 |
| GB | 862641 A | 3/1961 |
| WO | 0041754 A1 | 7/2000 |
| WO | 0119434 A1 | 3/2001 |
| WO | 02053214 A1 | 7/2002 |
| WO | 2002053214 | 7/2002 |
| WO | 2004002556 A1 | 1/2004 |
| WO | 2004078226 A2 | 9/2004 |
| WO | 2004078239 A1 | 9/2004 |
| WO | 2004078240 A2 | 9/2004 |
| WO | 2004089450 A1 | 10/2004 |
| WO | 2006024461 A1 | 3/2006 |
| WO | 2006039930 A1 | 4/2006 |
| WO | 2006077466 A2 | 7/2006 |
| WO | 2006084876 A1 | 8/2006 |
| WO | 2006086983 A1 | 8/2006 |
| WO | 2006089768 A1 | 8/2006 |
| WO | 2006130100 A1 | 12/2006 |
| WO | 2008031237 A1 | 3/2008 |
| WO | 2011039207 A1 | 4/2011 |
| WO | 2013170392 A1 | 11/2013 |
| WO | 2014117944 A1 | 8/2014 |
| WO | 2016016184 A1 | 2/2016 |
| WO | 2020026050 A1 | 2/2020 |

OTHER PUBLICATIONS

International Search Report and Written Opinion received for International Application No. PCT/IB2019/055547, mailed on Jul. 31, 2019, 9 pages.
"Link to Opposition of EP2814547", https://register.epo.org/application?number=EP13724506&lng=en&tab=doclist, accessed Apr. 26, 2017, 3 pages.
"U.S. Appl. No. 61/647,851, filed May 16, 2012 in the name of Jurg Hirschel".
"U.S. Appl. No. 12/403,849", Applicant's Response to Non-Final Office Action of Sep. 28, 2009, submitted on Feb. 26, 2010, 14 pages (w/EFS Acknowledgment).
"U.S. Appl. No. 12/403,849", USPTO Final Office Action dated May 27, 2010, 10 pages.
"International Preliminary Report on Patentability", Application No. PCT/CH2007/000241, Apr. 7, 2009, 15 pages.
"International Preliminary Report on Patentability", Application No. PCT/CH2013/000081, Nov. 18, 2014, 6 pages.
"International Search Report", Application No. PCT/CH2007/000241, Sep. 6, 2007, 6 pages.
"International Search Report and Written Opinion", Application No. PCT/CH2013/000081, Sep. 23, 2013, 11 pages.
"Written Opinion of the International Searching Authority", Application No. PCT/CH2007/000241, Mar. 15, 2009, 12 pages.
International Preliminary Report on Patentability received for International Application No. PCT/IB2019/055547 issued on Feb. 11, 2021, 8 pages.

* cited by examiner

C

B

A

PRIOR ART

PRIOR ART

PRIOR ART
Fig. 13c-1     Fig. 13b-1     Fig. 13a-1
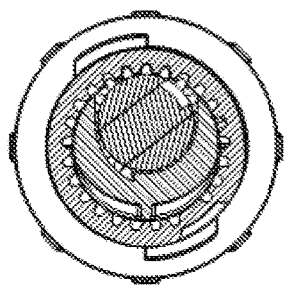 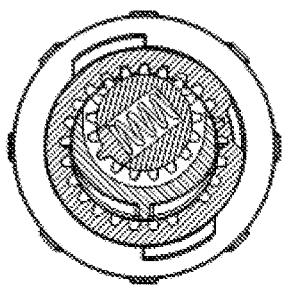 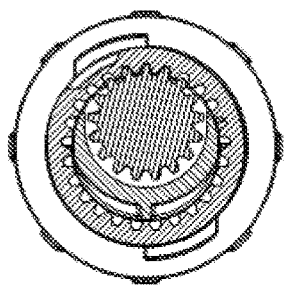
C     B     A
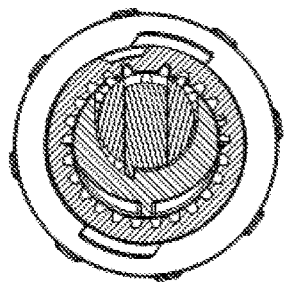 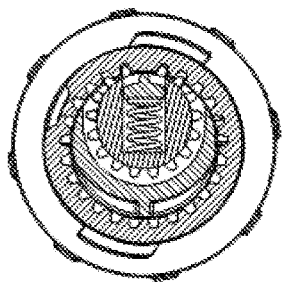 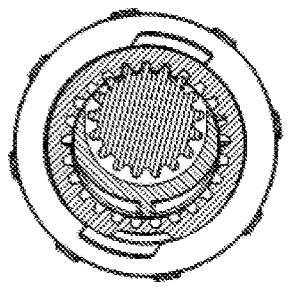
Fig. 13c-2     Fig. 13b-2     Fig. 13a-2

PRIOR ART

PRIOR ART

PRIOR ART

C

B

A

PRIOR ART

PRIOR ART

PRIOR ART

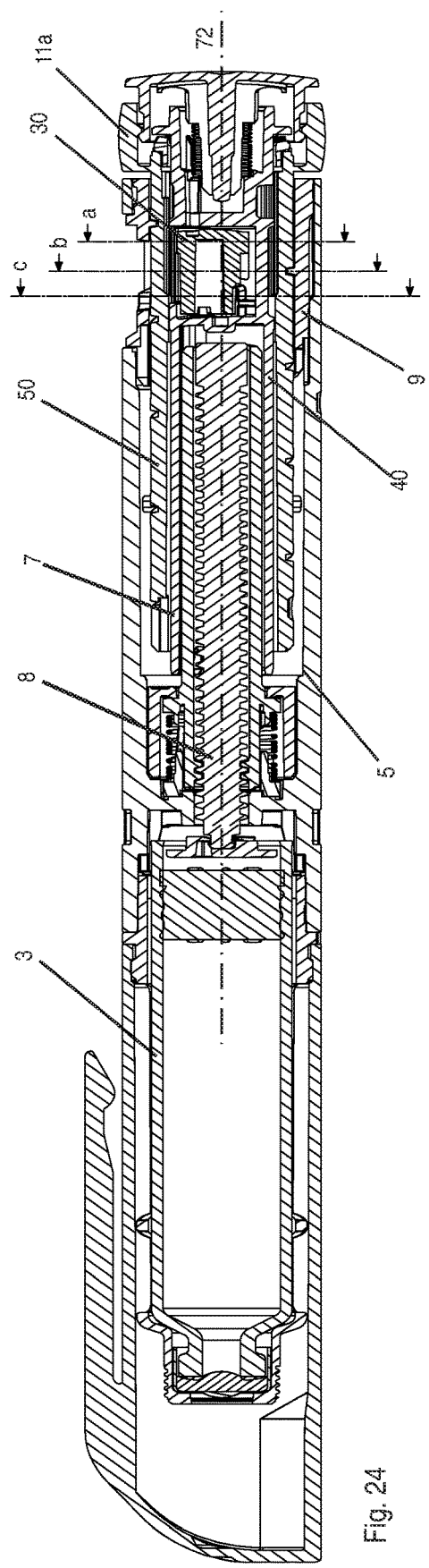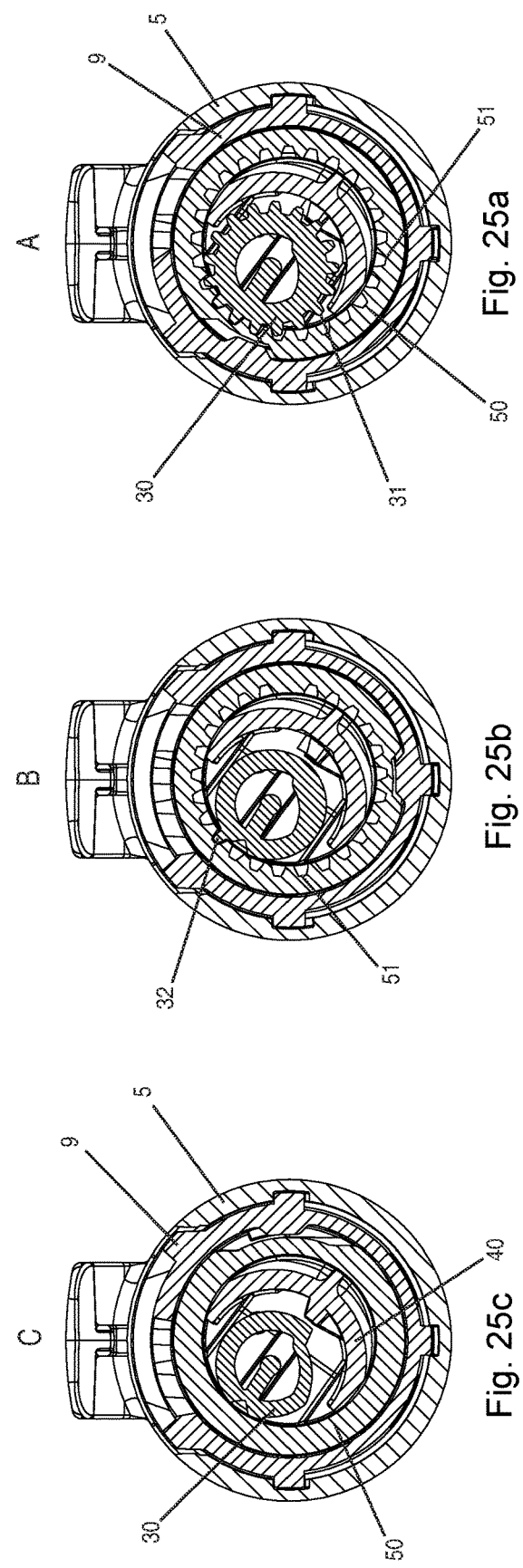

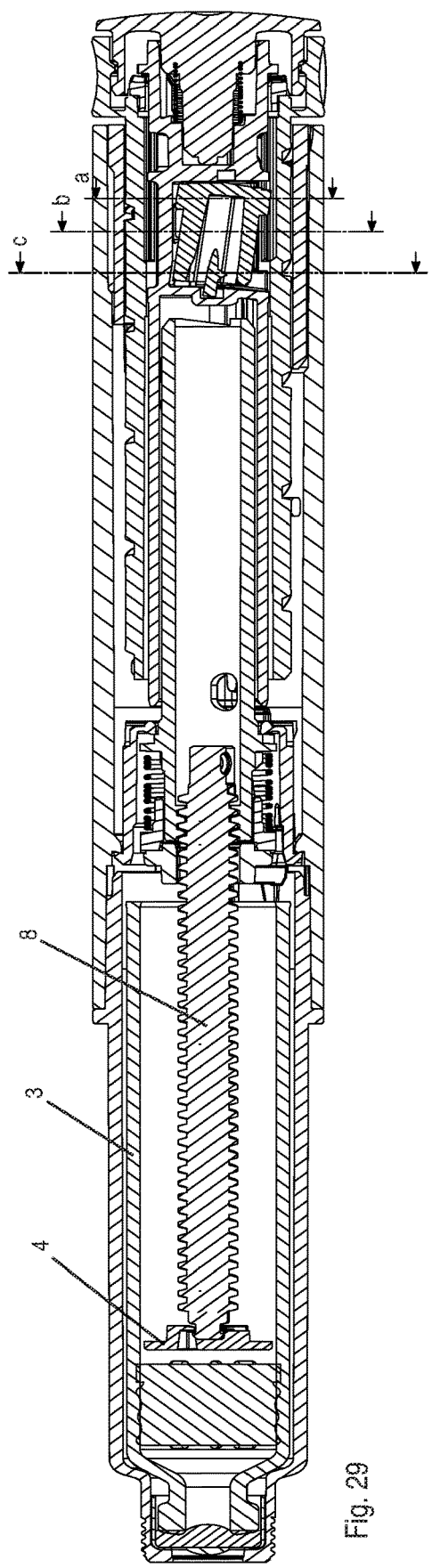
Fig. 29
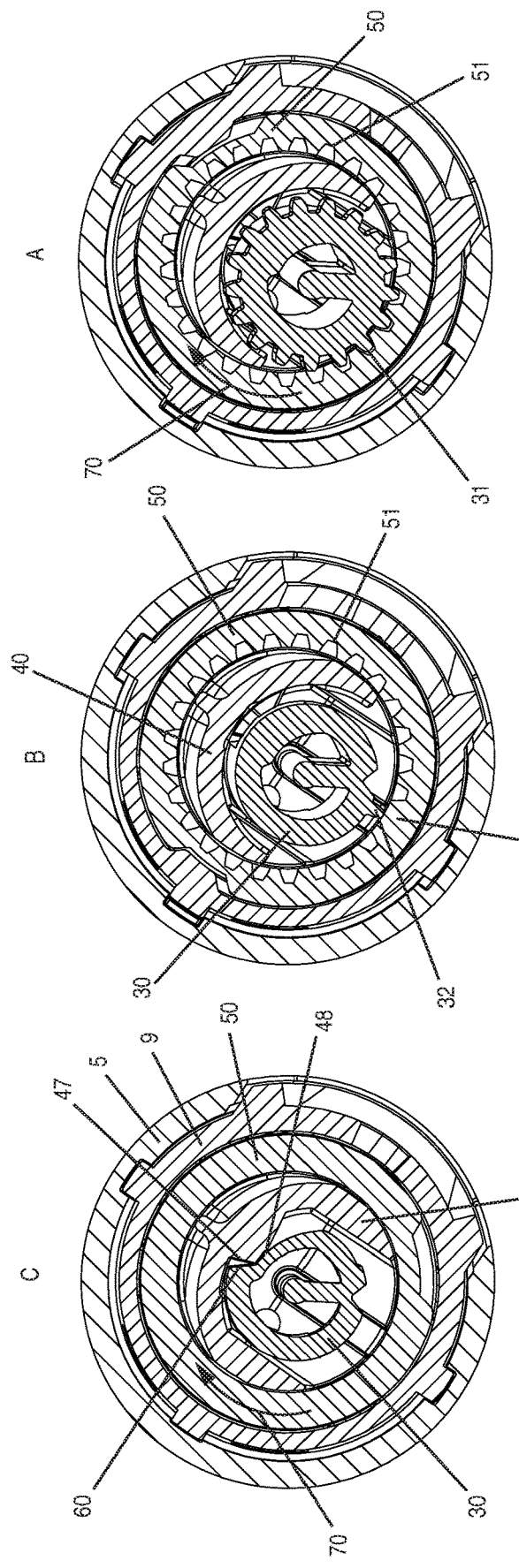
Fig. 30a
Fig. 30b
Fig. 30c

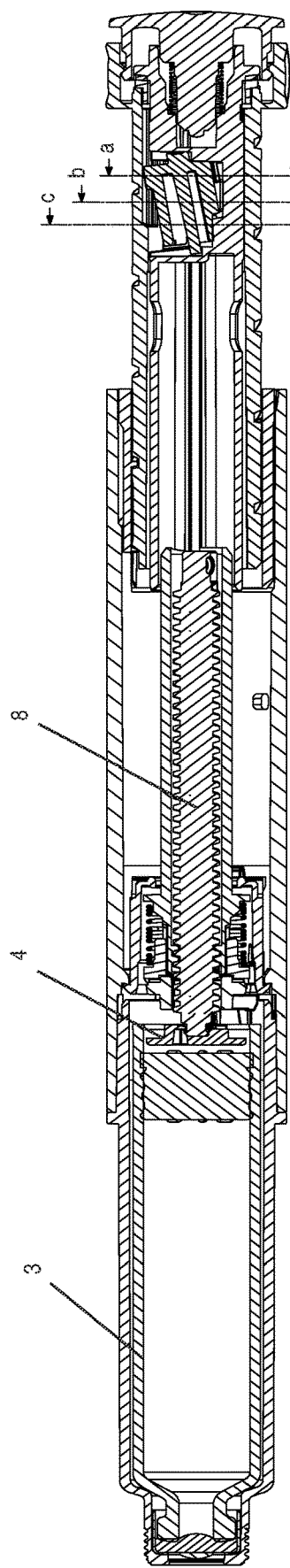
Fig. 31
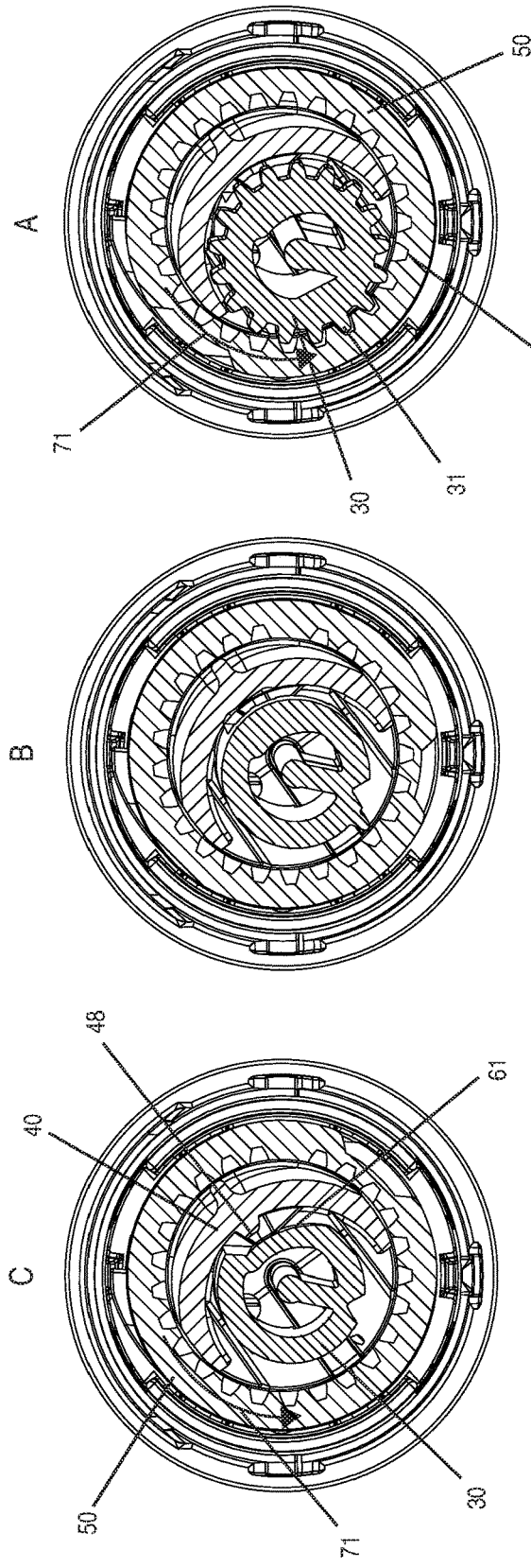
Fig. 32a
Fig. 32b
Fig. 32c

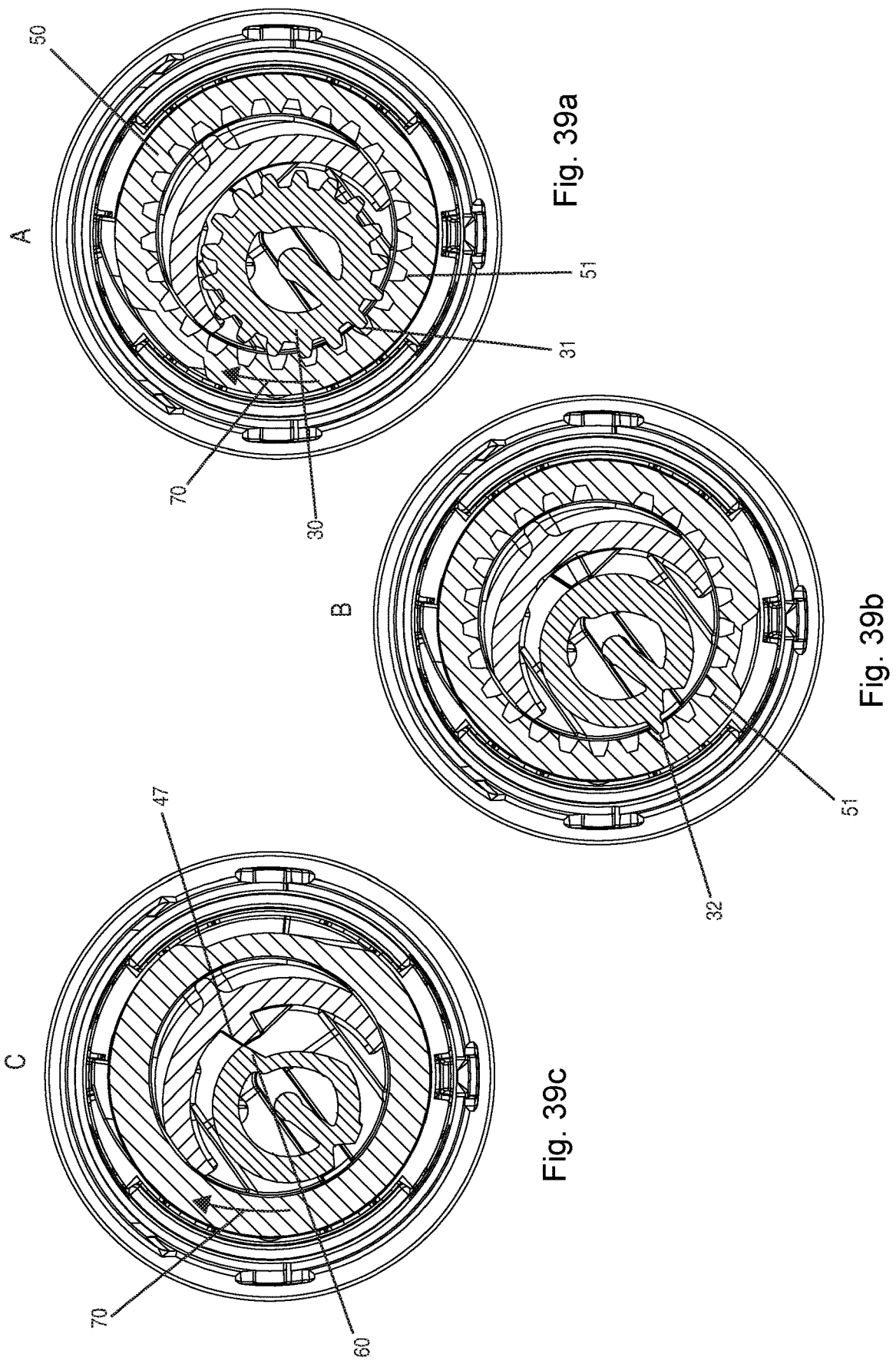

ALTERNATIVE DEVICE FOR ADJUSTING A DOSAGE WITH A LIMITING MECHANISM FOR A DEVICE FOR ADMINISTERING A PRODUCT

CROSS-REFERENCE TO RELATED APPLICATIONS

This application claims priority to International Patent Application No. PCT/IB2019/055547, filed Jul. 1, 2019, entitled "ALTERNATIVE DEVICE FOR ADJUSTING A DOSAGE WITH A LIMITING MECHANISM FOR A DEVICE FOR ADMINISTERING A PRODUCT," which in turn claims priority to European Patent Application No. 18186335.8, filed Jul. 30, 2018, entitled "ALTERNATIVE DEVICE FOR ADJUSTING A DOSAGE WITH A LIMITING MECHANISM FOR A DEVICE FOR ADMINISTERING A PRODUCT", each of which is incorporated by reference herein, in the entirety and for all purposes.

SPECIFICATION

The disclosure relates to an alternative for an improved device for adjusting a dosage in a device for administering a product, for example an injection syringe for insulin in the form of a pen-shaped syringe for self-administration of insulin, referred to as a pen. The disclosure further relates to a limiting mechanism that prevents the adjustment of a dosage to be administered past a predetermined value. As an example for the disclosure, but not restrictive to the applications in administration devices, examples of such devices are described in the published patent applications CH 703993 A2 and EP2814547A1.

In administration devices with product containers, e.g., an inserted cartridge that contains a product for several administrations, it is sometimes desirable to prevent a dosage from being preselected that exceeds the amount of product remaining in the cartridge. If such a dosage could be preselected, the user would assume that a corresponding dosage can be administered, whereas in fact only a part is administered. This is undesirable or even dangerous, depending on the situation.

A means for solving this problem known from prior art is to count or measure the total as the sum of the administered dosages, with a limit stop preventing a further ejection or dosage selection as soon as the total corresponds to the volume nominally contained in the cartridge.

A drive mechanism for medicine administration devices is described in the published patent application WO 2004/078226, for example. This drive mechanism contains a housing, a dosage-setting sleeve and a two-part piston. In one embodiment, a driver sleeve moves downward along an inner part of the piston rod when a dosage is selected. The distance traveled corresponds to the ejection stroke of the piston necessary for the dosage. When a subsequent dosage is selected, the driver sleeve moves farther along the piston rod. The position of the driver sleeve thus corresponds to the quantity of medication still contained in the cartridge. When the driver sleeve reaches the end of the thread on the inner part of the piston rod and therefore can no longer rotate, this corresponds to an empty cartridge.

Another example is described in the published U.S. Pat. No. 6,582,404, which shows a limiting mechanism for medication administration devices that prevents setting a dosage which exceeds the amount remaining in the cartridge. The administration device comprises a dosage-setting member which is moved away from a fixed limit stop by rotation relative to a driver, when setting a dosage. The dosage-setting member is connected to the driver in such a manner that the former can be turned in one direction without moving the latter. The dosage is administered by turning back the dosage-setting member and thereby moving the driver. The rotating driver causes an ejection motion of the piston rod. The driver is provided with a track, the length of which corresponds to the quantity of medication contained in the cartridge. A track follower, which is connected to the dosage-setting member, runs in this track. Every time a dosage is selected, the track follower moves farther in the track. When the track follower reaches the end of the track, the dosage-setting member cannot be turned further and setting a dosage beyond the amount still remaining in the cartridge is prevented.

Another example of such a device is described in EP 0554996 and shows an injection device for administering liquids such as insulin into bodily tissue. This injection device contains a dosage-setting mechanism having a 1-ring and a 10-ring. A transmission member is provided for selectively coupling the one ring to the other so that they turn together only in selected sections during the dosage-setting. The set dosage is displayed by means of digits on the rings. The injection device further comprises a dosage-limiting mechanism, which limits the movement of a guide spindle for the intended piston motion in the cartridge, wherein projections in the plunger reach the end of grooves along the guide spindle and prevent a further movement. The dosage-limiting mechanism is provided separately from the dosage-setting mechanism.

WO 2006/086983 shows an example of a dosage-setting device for self-injection devices with a dosage-limiting mechanism having two rotating parts, wherein the first part turns continually while setting a dosage and the second part only turns part of the time by a selective coupling device after a defined rotational position has been reached. This has the effect that the second part turns discontinuously over a smaller angle than the first part. The rotation of the second part is then limited by a limit stop fixed to the housing, which prevents a dosage setting exceeding the remaining amount still present in the cartridge.

In EP2814547A1 an improved device for adjusting a dosage with a limiting mechanism is presented which can be used in an injection or administration device. During dose setting, a stop wheel is rotated by a dose sleeve with a defined transmission ratio. After a defined number of revolutions, the stop wheel is tilted by stop means present on the dose sleeve and the stop wheel that mutually abut each other in a stop position. The stop wheel is tilted against an elastic force that is provided by a shaft that is part of the stop wheel. When the stop wheel is tilted, further dose setting in a dial up direction (increasing a dose or dosing up) is prevented, whereas a dial down movement (dose correction or dosing down) is still allowed. During dial down, the stop wheel moves back to the non-tilted position due to the elastic forces provided by the shaft. The stop wheel with the elastic shaft has a complicated design and is demanding for the properties the wheel is made of. As a preferred embodiment, a gear guidance is presented which returns the stop wheel in the non-tilted position during dial down dosing only, e.g., the elastic forces are still required for returning the stop wheel during any adverse tilting movements of the stop wheel during dial up dosing movements. The EP2814547A1 application is incorporated in the present application as a comparative prior art example.

Finally, in EP 2918298, a stop mechanism is presented based on the tilting of a stop wheel, comparable to the EP2814547A1, e.g. in the stop position the stop wheel is forced to be tilted to prevent further dose setting. No elastic forces are used to return the stop wheel in the non-tilted position, but another gear guidance is used to return the stop wheel during dial up dosing only.

It is an objective of the present disclosure to overcome the drawbacks of the prior art and provide a space saving dosage limiting mechanism that is reliable and simple and prevents the setting of a dosage beyond a predetermined value; an alternative limiting mechanism is presented compared to the prior art with the stop wheel having the elastic shaft presented above.

This objective is solved by the subject matter disclosed, in that the return of the stop wheel from the tilted position to the non-tilted position is accomplished using two gear guidances without the need for an elastic shaft or an elastic element such as a spring. The two gear guidances return the stop wheel from a tilted to a non-tilted position both during dial up and dial down dosing movements. In another aspect of the present disclosure, an injection device comprising the limiting mechanism and a receptacle with medication is presented wherein the limiting mechanism limits the dose setting to the total amount of medication present in the receptacle, e.g., the limiting mechanism counts and accumulates doses set and injected during repeated dose settings and prevents a final dosage being set that is above the remaining amount of medication left in the receptacle.

DESCRIPTION

The term "medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The EP2814547A1 application is incorporated below in the present application as a comparative prior art example.

Various indications of directions and positions are made in the present description, which will be briefly explained at this point. "Axial orientation" means an orientation along the longitudinal axis of an administration device or of some other device. "Distal" refers to the end of the administration device at which the product or medication exits. Accordingly, "proximal" refers to the opposite end of the administration device. "In the distal direction" means viewed in the direction of the distal end and "in the proximal direction" analogously means viewed in the direction of the proximal end.

The disclosure presented in EP2814547 relates, for example, to an improved injection device for administering a fluid product. Such an injection device comprises a housing with a receptacle for the product, a conveying unit for conveying the product and a dosing device for setting a product dosage to be administered and for displaying the set product dosage. The housing forms a receptacle for the product, preferably a receptacle for a container filled with the product. This container can be a cartridge for example. The conveying unit comprises a piston rod, which is movable relative to the housing in a conveyance direction in order to eject the set product dosage in a conveyance stroke corresponding to the set product dosage. The conveyance stroke is a translational movement of the piston rod, preferably a linear pushing movement. In a preferred embodiment, a movable piston of the container constructed as a cartridge is displaced in the conveyance stroke. The conveying unit further comprises a guide element, which guides the translational movement of the piston rod. In a preferred embodiment, the guide element is constructed as a longitudinal guide for the piston rod, fixed relative to the housing, so that the piston rod can be displaced relative to the guide element but cannot be rotated. The conveying unit further comprises a drive element that is engaged with the piston rod. The drive element in an example is constructed as a threaded nut, the inside thread of which is brought into engagement with a corresponding outside thread applied to the outer surface of the piston rod. The threaded nut is preferably mounted in the housing rotatably, but axially fixedly. In a possible preferred embodiment, the following kinematic arrangement results for the conveying mechanism of the conveying unit: a rotation of the axially fixed threaded nut relative to the piston rod results in an axial movement of the piston rod, because it cannot rotate relative to the housing due to the longitudinal guide. In other embodiments, likewise possibly preferred, the kinematic arrangement can also be inverted. This is effected via a so-called kinematic inversion, wherein the threaded nut is rotationally fixed relative to the housing and the longitudinal guide is rotatable relative to the housing and also movably mounted. If the longitudinal guide is rotated with this kinematic inversion, then the piston rod screws, due to the threading of the threaded nut, which is rotationally fixed relative to the housing in this case.

The dosing device of the injection device comprises a dosage-setting member, preferably a dosing sleeve, which is in threaded engagement with the inside of the housing. A grippable element, which allows setting of a desired dosage by the user, is mounted at the proximal end of the dosage-setting member. When the dosage to be administered is increased, the dosage-setting member preferably undergoes a turning movement out of the injection device. To administer the set dosage or to reduce a dosage that may have been set too high, the dosage-setting member can then be screwed back into the injection device. In another preferred embodiment, there is a non-self-locking threaded connection between the housing and the dosage-setting member configured as a dosing sleeve, so that the dosing sleeve can be screwed back into the injection device by exerting axial forces.

The dosing device further comprises a coupling device, which can operatively connect the dosing device to the conveying device. The coupling device is designed in such a manner that a dosage to be administered can be set and/or corrected independently of the conveying device and that the dosing device can be selectively operatively coupled to the conveying device during the administration of the dosage, so that a movement of the dosing device is transferred completely or proportionally to the conveying device as an ejection movement. For example, only the rotational portion of a screw movement of a dosing sleeve, or alternatively only the axial displacement thereof, can be transferred to the conveying device. In one embodiment, the coupling device comprises a coupling sleeve with a coupling surface, wherein the coupling surface has engagement elements. The dosage-setting member constructed as a dosing sleeve has a counter-coupling surface with counter-engagement elements. The coupling surface and the counter-coupling surface can be brought into engagement with one another by a coupling movement and a relative movement between the coupling and the dosing sleeve can thus be suppressed.

The dosing device further comprises an ejection button, which is movably mounted at the proximal end of the dosing device. In a preferred embodiment of the dosage-setting member as a dosing sleeve, the ejection button is mounted coaxially with the dosing sleeve at the proximal end thereof. Preferably, the button is rotatable with respect to the dosing sleeve and is mounted with a certain axial movability. In a preferred embodiment, the coupling sleeve is also arranged coaxially with the dosing sleeve, the coupling sleeve preferably being arranged at least in part inside the dosing sleeve. In this embodiment, the coupling surface is arranged as an annular flange on the outer surface of the sleeve in the proximal area thereof. Complementarily, the counter-coupling surface is also arranged on the inside of the dosing sleeve. In one possible embodiment, the engagement elements and the counter-engagement element are oriented axially relative to the injection device so that in this case the coupling movement is an axial movement. For example, the coupling engagement can be created by pressing the ejection button. The arrangement of the dosing sleeve, coupling sleeve and ejection button can further comprise a spring, which holds the coupling surface and the counter-coupling surface in engagement. The dosing sleeve and the coupling sleeve move jointly axially during a dosing movement, wherein a rotation relative to one another is possible as long as the ejection button is not pressed and therefore the coupling is not locked.

In one embodiment in a comparative example, the coupling sleeve is rotationally secured relative to the threaded nut, but axially movable. This embodiment allows an axial movement of the coupling sleeve relative to the threaded nut. If the coupling is locked by pressure on the ejection button and the dosing sleeve is screwed into the injection device, then the coupling sleeve follows this movement. Due to the rotational locking of the threaded nut, the rotation is only transmitted to the threaded nut, and consequently the piston rod is axially moved.

In order to ensure that the drive element constructed as a threaded nut can rotate only in the direction that results in a movement of the piston rod in the ejection direction, i.e., in the direction causing an ejection, a so-called reverse rotation lock is preferably provided between the housing and the threaded nut. This can be a radially directed or an axially directed reverse rotation lock. The reverse rotation lock is preferably constructed by a formfitting means in such a manner that a rotation of the threaded nut contrary to the ejection direction is completely blocked. For rotation in the ejection direction, the reverse rotation lock preferably has a certain resistance, also known as reluctance, due to a frictionally engaging means, which must be overcome in order to bring about a movement of the threaded nut. This is advantageous in order to prevent an undesired ejection when correcting an excessively high dosage. Preferably, the rotation resistances of the reverse rotation lock and the coupling are matched to one another.

According to a first aspect in the comparative example, the dosing device according to the disclosure has a limiting mechanism containing the following parts:

a first limiting means with a first stop means or stop adapted in such a manner that the limiting means follows a movement of the dosage-setting member during the dosing movement, and a second limiting means with a second stop means or stop adapted in such a manner that the second limiting means continuously follows a movement of the first limiting means during the dosing movement proportionally with a defined transmission ratio, and during an ejection movement does not undergo any relative movement with respect to the first limiting means.

The first and the second stop means each describe a path curve in such a manner by their movements that the two path curves intersect in at least one point or come so close together that the stop means strike against one another, whereby a blocking of the movement and the dosing movement can be effected. Preferably the stop means move at identical speed on different-length path curves, or at different speeds on equal-length path curves, wherein closed path curves can be passed through by one or both stop means, preferably several times, or partially until the stop means strike one another at a limit stop position.

The first limiting means can be constructed preferably on an inner axial wall section of the dosing sleeve as a circumferential toothing consisting of teeth and teeth interstices. The first stop means is constructed as a wedge which fills out a tooth interstice in a part of the wall section and thus interrupts the circumferential toothing. This section is referred to as a stop zone and the section with freely running toothing as a drive zone.

The second limiting means can be constructed as a sleeve-like stop wheel with distally and proximally projecting axial ends of a rotational shaft, wherein the rotational shaft is held by a spoke or spoke means, which can also be constructed as a continuous wall in the interior of the stop wheel. Circumferential toothing consisting of teeth and teeth interstices is constructed on an outer wall section of the stop wheel. The second stop means is formed on the outer wall section of the stop wheel by a rib that extends one of the teeth in the axial direction. The second limiting element or stop wheel is also axially arranged in such a manner that its circumferential toothing meshes with the circumferential toothing of the first limiting means in the area of the drive zone, and the rib is moved in the area of the stop zone. The shaft ends are rotatably received by bearing points in the coupling sleeve so that the stop wheel, operatively connected positively in the toothing, can rotate about its own axis parallel to the common rotational axis of the dosing sleeve and the coupling sleeve.

The first stop means moves on a circular path curve during a dosing movement, due to the relative movement of the dosing sleeve and the coupling sleeve, and the second stop means moves on a path curve that can be circular. If there is a lack of relative movement of the dosing sleeve and the coupling sleeve during an ejection movement, the stop means do not move against one another on these curves. Suitable selection of the dimensions and the transmission ratio can have the effect that the stop means pass through their path curves several times until, starting from a stop position, they again contact one another at the stop position. These distances or this angle of rotation from stop position to stop position can be referred to as periods.

Such a period results mathematically from the least common multiple (LCM) of the numerator and denominator of the transmission ratio. Therefore, it turns out that the period can advantageously have large values if at least the numerator or the denominator is selected as a prime number. Thus appropriately long paths or angles of rotation can be dimensioned or limited with simultaneously high resolution and a compact construction, because the path curves can be run through several times. For example, by suitable selection of a starting position inside a period, any desired distance of rotation that must be run through until the stop position is reached can be defined. By suitable selection of the initial position for the stop wheel, the dosage limitation can be programmed to any desired number of fractions of tooth pitches or rotations inside a period, without structural changes to the design form being necessary. In a preferred embodiment, such a distance can correspond to the amount of medication nominally contained in the cartridge. Every time a dosing movement takes place, the stop means run relative to one another on their path curves and can thus reach their stop position. Thereby the dosing sleeve cannot turn farther in the dosage-increasing direction and a dosage setting exceeding the remainder still present in the cartridge is prevented. In a preferred embodiment this is achieved directly by virtue of the fact that, by contacting one another, the stop means prevent further movement of the two limiting means in the limit stop direction. On the other hand, it is possible to leave the stop position at any time by reversing the movement, in which case the dosing sleeve turns in the dosage-reducing direction.

In another example according to a second aspect, such a prevention of further movement of the two limiting means can also be done indirectly by means of a force that appears in the mutual striking of the two stop means against an elastic restoring force and/or via a gearing means that brings a first limit stop means on the coupling sleeve into engagement with a second limit stop means on the second limiting means. In a preferred embodiment, a radial limit stop can be formed, preferably integrally, on the second limit stop means, on an outer wall section of the stop wheel. This axial section is called a limit stop zone. The force acting between the two stop means is able to deform the rotational axis and/or the spoke means on the stop wheel elastically, whereby the stop wheel is translated or pivoted transversely to its axis of rotation. In the process, the second limit stop means comes into operative connection with the first limit stop means, which is applied in the area of the limit stop zone on the coupling sleeve. This operative connection can be configured as a friction fit or a form fit, as a counter-radial stop on the coupling sleeve in a preferred embodiment, and prevents further relative rotation of the stop wheel in the dosage-increasing direction relative to the coupling sleeve, which in turn cannot turn in the dosage-increasing direction due to the reverse rotation lock. In another preferred embodiment, the second limit stop means can also be supported in a transverse guide in the stop wheel movably in the transverse direction and fixed rotationally and axially relative to the rotational axis of the stop wheel, and can be held in its normal position by a spring means. This second limit stop means extends axially past the limit stop zone and the stop zone. The second stop means is applied in the area of the stop zone on the second limit stop means opposite the radial limit stop, which can extend past the limit stop zone. Instead of returning the second limit stop means from its stop position into its normal position by means of a spring means, this can be effected in another preferred embodiment by a gear guidance, which borders on the radial limit stop as a curved surface on the coupling sleeve in the limit stop zone and moves the second limit stop means radially in its transverse guide during return rotation of the stop wheel, in which case the dosing sleeve turns in the dosage-reducing direction.

As an additional safety aspect, the axial movement of the piston rod, the conveyance stroke, can be blocked when the maximum conveyable product quantity has been reached. For this purpose, at least one limit stop, which comes into engagement with a counter-limit stop on the drive element as soon as the maximum conveyable product amount has been conveyed out of the injection device, can be arranged at the proximal end of the piston rod. The limit stop and the counter-limit stop can act radially, i.e., perpendicular to the longitudinal axis of the injection device, due to end of threads. Alternatively, the limit stop and the counter-limit stop can also act axially, i.e., parallel to the longitudinal axis of the injection device. Axial and radial actions can also be combined in advantageous embodiments.

The comparative example described above describes how the stop wheel can also be returned to the non-tilted position using a single gear guidance during dose reduction (dial down movements). A general description of the present disclosure appears in the following.

In a first aspect an embodiment according to the present disclosure is presented which works analogous to the comparative example described above, in that the tilting of a stop wheel is used to prevent further dose setting. Presented is a dosing device for an administration device with a limiting mechanism comprising a sleeve like dosing member defining a first longitudinal axis with an inner wall, an outer wall and having a toothing and a first stop means positioned on the inner wall. The outer wall of the dosing member may comprise a threading for threaded engagement to a housing or housing part of the dosing device. In case of a threaded engagement, the dosing member performs a helical movement with respect to the housing upon rotation of the dosing member during dose setting and dose correction. During dose delivery, the dosing member is returned into the housing, for example by pushing a dose button by the user. The movement back into the housing is coupled to a conveying mechanism which ensures that a piston rod is advanced and the set dosage is injected. Alternatively, the dosing member has on the outer wall a protrusion or any other means that prevents an axial movement with respect to the housing during dose setting, dose correction and dose injection. During dose setting the dosing member is rotated without axial translation, and a resilient member, for example a helical spring or a coil spring, is wound up and the energy stored in the resilient member is released and coupled to the conveying mechanism during dose delivery.

The dosing device further comprises a coupling sleeve coaxially arranged within the dosing member, and the coupling sleeve is rotatable around the first longitudinal axis relative to the dosing member during dosing movements. Relative rotation means that either the dosing member is rotatable relative to a non-rotatable coupling sleeve or, vice versa, the coupling sleeve rotates relative to a non-rotating dosing member. The coupling sleeve is rotationally coupled to the dosing member during dose delivery. Preferably, the coupling sleeve does not rotate during dose setting movements, since the coupling sleeve is indirectly or directly coupled to a housing or housing insert of the dosing mechanism. For example the coupling sleeve is coupled to the housing via a one way ratchet or clutch having teeth and counter teeth that are oriented parallel to the housing or are oriented in a radial direction. As an alternative, the coupling sleeve is directly or indirectly coupled to the housing via a friction clutch mechanism.

The dosing device comprises a stop wheel having a toothing on the outside that meshes with the toothing of the dosing member. The stop wheel may be sleeve-like and defines a second longitudinal axis. The stop wheel has a second stop means and is rotatably received in the coupling sleeve by at least one bearing point in the coupling sleeve. The stop wheel can move from a first position wherein the first and second longitudinal axis are arranged parallel to another (the non-tilted position) to a second position where the second longitudinal axis is tilted with respect to the first longitudinal axis (the tilted position).

During dosing movements, the dosing member is rotated in a first direction with respect to the coupling sleeve for dial up, and in a second rotation direction which is opposite to the first rotation direction for dial down. Dial up represents thus increasing of a dose or dosing up and dial down decreasing of a dose or dosing down. The set dose can preferably be viewed on digits printed onto the outside wall of the dosing member through a viewing window in the housing. The stop wheel follows the dosing movements of the dosing member with a defined transmission ratio, preferably the stop wheel rotates at a higher rotational frequency compared to the dosing member. The complementary toothings of the stop wheel and the dosing member are in a meshed engagement and the transmission ratio is defined by the different number of teeth on the stop wheel and the dosing member respectively. Preferably the dosing member and the stop wheel rotate in the same rotation direction; alternatively both rotate in opposite rotation directions, for example if an additional gear wheel is arranged between the stop wheel and the dosing member.

The first and second stop means or stops each describe path curves during dose setting in such a manner that the two path curves come so close together that the first and second stop means or stops contact one another in a stop position. Preferably the path curves of the first and second stop means or stops are closed and circular shaped.

During dose delivery, the stop wheel does not move relative to the dosing member. Preferably, during dose delivery the dosing member, the stop wheel and the coupling sleeve rotate together.

The dosing device is further characterized by a first gear guidance that is arranged, or structurally or functionally positioned between the coupling sleeve and the stop wheel. The first gear guidance is configured to move the stop wheel from the second (tilted) position back to the first (non-tilted) position during dial up when the first and second stop means are not in the stop position. The first gear guidance may move the stop wheel back to the first position when the stop wheel is partially tilted between the first and second positions, or out of the first position. The stop wheel may be inadvertently moved from the first position to the second position and the first gear guidance ensures that the stop wheel is returned to the non-tilted position by the first gear guidance. The dosing device has a second gear guidance which is arranged between the coupling sleeve and the stop wheel and which is configured to move the stop wheel from the second position back to the first position during dial down movements, e.g., if a dose is decreased during dose setting. The advantage of using a gear guidances is that no additional parts, such as a spring member or complicated resilient structures are required to return the stop wheel to the first position. The advantage of having two gear guidances is that both during dial up (dosing up) and dial down (dosing down) the stop wheel is immediately returned to the non-tilted position when the first and second stop means are not in the stop position. Thus, any unintended tilting of the stop wheel is immediately corrected during dial up movements or dial down movements which increases the reliability of the dosing device. The first and second gear guidance may be located adjacent to another. Alternatively, more than two, e.g., a plurality of gear guidances may be used.

The respective path curves of the first and second stop means are closed and can be run through multiple times by the first and second stop means during dosing movements until the stop means contact one another at the stop position, and thereby moving the stop wheel from the first to the second position and preventing the first gear guidance from moving the stop wheel back to the first position and thereby blocking dial up dosing movements. During repeated dose setting the stop wheel may inadvertently move from the first to the second position and the first gear guidance (during dial up) and the second gear guidance (during dial down) ensures that the stop wheel is returned to the first, non-tilted position. The stop wheel may move to, or partially move towards, the second position due to impact, acceleration or gravitational forces acting on the mechanism. On the other hand when the stop means interact with each other in the stop position, the stop wheel is forced to move into the second position and, due to the engaging stop means, the first gear guidance cannot return the stop wheel back to the first position during dial up movements. As a consequence, the mutual shifting of the sliding surfaces of the gear guidance that are arranged between the coupling sleeve and the stop wheel is prevented and thereby the stop wheel cannot move back to the first position. The dosing up movement of the dosing member with its internal toothing meshing with the external toothing of the stop wheel is, thereby, blocked as well. During a dial down movement the stop means get out of engagement, e.g., do not contact each other anymore, and subsequently the second gear guidance is not hindered to move the stop wheel from the second position to the first position. The second gear guidance is designed to allow the stop means to get out of the mutual engagement, for example by shallow sloped surfaces that interact, followed by a more steep interaction to displace the stop wheel into the first position. The gear guidance may have a continuous variation of slopes.

The dosing device wherein the toothing on the inner wall of the sleeve like dosing member comprises teeth and teeth interstices and wherein the first stop means is formed as a wedge that fills out at least a part of a between-teeth interstice.

The dosing device wherein the second stop means is formed as a rib on the outside of the stop wheel. Preferably, the rib is formed as an extended tooth of the circumferential toothing present on the outside of the stop wheel.

The dosing device may be formed according to any of the previous embodiments, including those in appended claims, wherein the coupling sleeve is directly or indirectly rotationally coupled or couplable to the housing of the dosing device via a one-way ratchet. The one-way ratchet prevents the coupling sleeve from rotation in the dial up rotation direction and allows for rotation of the coupling sleeve in the dial down rotation direction. In the dial down rotation direction, the one-way ratchet provides for a certain threshold torque that needs to be overcome before the coupling sleeve may rotate in that direction; this ensures that the coupling sleeve does not rotate during dial down movements of the dosing member during dose setting but allows for rotation of the coupling sleeve during dose delivery. The one-way ratchet may be an axial ratchet (oriented parallel to the first longitudinal axis) or a radial ratchet (oriented perpendicular to the first longitudinal axis). The ratchet may comprise asymmetric saw teeth and/or resilient arm(s) located on the housing or a housing part of the dosing device and on a ratchet member that is preferably biased by a spring member or a resilient arm.

The stop wheel of the dosing device preferably comprises two shaft ends arranged along the second longitudinal axis and wherein one of the two shaft ends is rotatably received in a bearing or support located at the center of the coupling sleeve. The two shaft ends are integrally formed with the stop wheel and are rigid, e.g., non-resilient and not intended for elastic deformation. Preferably the other shaft of the two shaft ends is axially guided by the coupling sleeve in a direction perpendicular to the second longitudinal axis. The other shaft end is preferably guided in a recessed section of the coupling sleeve that is transversally oriented. The fact that one bearing point is fixed whereas the other shaft end can slide ensures that the stop wheel as a unit can tilt. Alternatively, the stop wheel has one shaft end received by a bearing point in the coupling sleeve and this bearing point is adapted to control the tilting or pivoting movement of the stop wheel when the stop means contact each other in the stop position.

The dosing member surrounds the stop wheel at least in part or is adjacent thereto and wherein the second longitudinal axis of the stop wheel is parallel and offset to the first longitudinal axis of the dosing member when the stop wheel is in the first position.

The stop wheel has an outer surface which is axially subdivided along the second longitudinal axis into at least three regions wherein the circumferential toothing on the outside of the stop wheel is located in a first region of the at least three regions, and wherein the second stop means is located in a region adjacent to the first region, and wherein the first and second gear guidances or elements thereof are located in a third region that is adjacent to the second region. The second stop means is located between the circumferential toothing and elements of the first and second gear guidances, e.g., sloped surfaces that will be discussed below.

The first gear guidance is formed by a first sloped or curved surface on the stop wheel and a complementary second sloped or curved surface on the coupling sleeve. During dial up movement of the dosing member, the curved or sloped surface on the stop wheel abuts and may slide or is slidable along the second curved or sloped surface of the coupling sleeve when the stop wheel is in the second position, or out of the first position (e.g., an intermediate position between the first and second position). During dial up movement, the dosing member and the stop wheel rotate with respect to the non-rotating coupling sleeve. Thus the first sloped or curved surface rotationally approaches the second sloped or curved surface on the coupling sleeve. When the two sloped or curved surfaces contact each other, the relative rotational movement is translated by the first gear guidance into a shift of the stop wheel with respect to the coupling sleeve during dial up movements. The return movement of the stop wheel to the first position is required to prevent blocking of the dosing member during dial up rotation of the member.

The second gear guidance is formed by a third sloped or curved surface on the stop wheel and a complementary fourth sloped or curved surface on the coupling sleeve. During dial down movement of the dosing member, the third curved or sloped surface on the stop wheel abuts and slides along the fourth curved or sloped surface of the coupling sleeve when the stop wheel is in the second position or out of the first position (e.g., at an intermediate position between the first and second position). During dial down movement, the dosing member and stop wheel rotate with respect to the non-rotating coupling sleeve. The third sloped or curved surface rotationally approaches and abuts the fourth curved or sloped surface on the coupling sleeve such that the third sloped surface of the stop wheel can slide and move along the fourth sloped or curved surface of the coupling sleeve. The sliding movement ensures that the stop wheel moves from the second to the first position during dial down movement. During dial up or dial down movements, torque will be transmitted from the stop wheel (dosing member) towards the coupling sleeve via the first and second gear guidances respectively. The one-way ratchet rotationally coupling the coupling sleeve to the housing is designed such that parasitic torques that are transmitted to the coupling sleeve while returning the stop wheel to the first position are below the threshold torque or resilience for rotating the coupling sleeve.

The dosing device may comprise a configuration wherein the first stop means of the dosing member moves on a circular path curve and whereby the stop wheel is axially arranged in such a manner that its toothing on the outside meshes with the toothing on the inner wall of the dosing member. The stop of the second stop means move on its path curve due to the relative movement between the dosing member and the coupling sleeve during dosing movements. The second stop means is part of the stop wheel and the stop wheel is driven on a circular path curve due to the meshed toothings such that the second stop means is driven on a circular path as well.

The disclosure further comprises an injection device with a cartridge (or receptacle) for the product, a conveying device for conveying the product, the conveying device comprising a piston rod which is moveable in a conveyance direction, preferably with respect to the housing of the dosing device, in order to eject the set product dosage in a conveyance stroke corresponding to the set product dosage. The injection device comprises the dosing device according to the embodiment described above, for setting a product dosage to be administered and for displaying the set product dosage. The cartridge for the product is preferably attached or attachable to the dosing device, preferably to the housing of the dosing device, using a cartridge holder. The dosing device, the conveying device, the housing of the dosing device, the cartridge and the cartridge holder are preferably aligned along the first longitudinal axis.

The coupling sleeve of the dosing device can operatively connect the dosing device to the conveying device, wherein the coupling sleeve is designed such that a dosage to be administered can be set and/or corrected independently from the conveying device and that the dosing device can be selectively, operatively coupled to the conveying device during the administration of the dosage.

The injection device may comprise a configuration wherein the setting of a dose beyond the amount of product left in the receptacle is prevented when the stop means contact one another at the stop position thereby moving the stop wheel from the first to the second position and preventing the first gear guidance from moving the stop wheel back to the first position and blocking dial up dose setting movements. A cartridge (receptacle) for a medicament may have a volume large enough to set and inject a number of consecutive doses. During each dose setting step, the stop wheel is moved to another position on its path curve (or relative to the dosing member) until both stop means contact one another in the stop position, thereby preventing further dose setting. The dosage set in the stop position is the last dose that may be injected and therefore the dose setting mechanism prevents setting a dose that is above the amount of medication left in the receptacle.

Further aspects and arrangements of embodiments according to the disclosure are presented in the descriptions of the figures.

DESCRIPTION OF THE DRAWINGS

Various embodiments will be explained below with reference to figures. A person skilled in the art will accordingly recognize that various changes and modifications can be made to the embodiments displayed below without deviating from the spirit of the disclosure or leaving its scope.

LIST OF THE DRAWINGS

Figure 1:
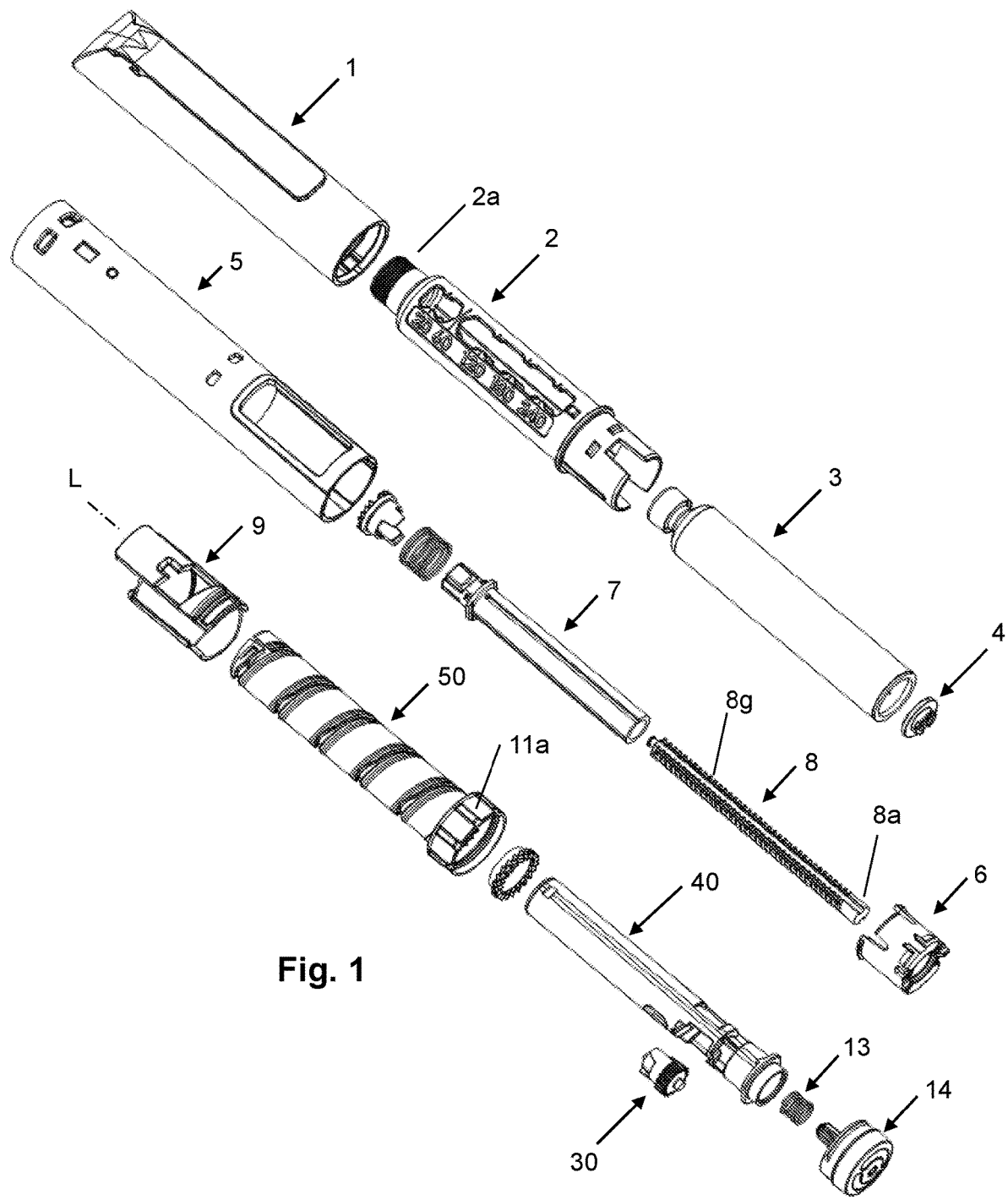

FIG. 1 is an exploded view of the individual parts of a first comparative example of an injection device according to the prior art.

Figure 2A:
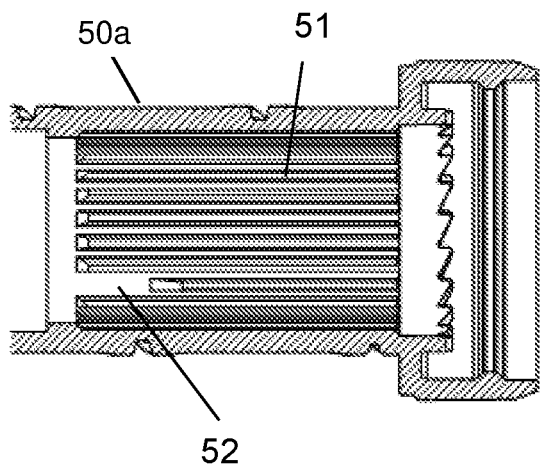
Figure 2B:
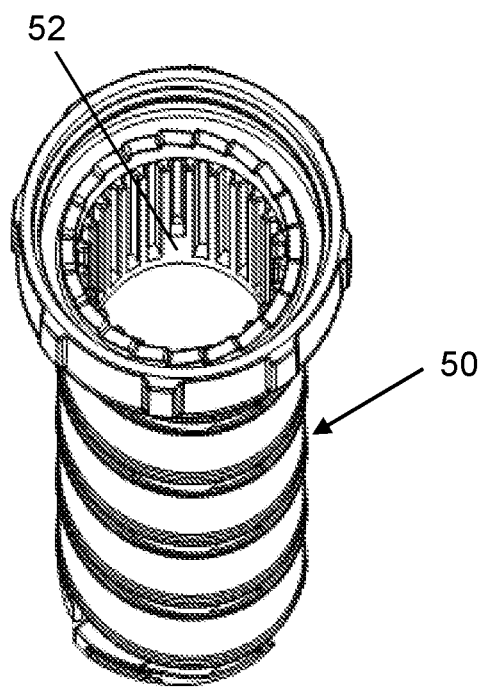

FIGS. 2a and 2b are a longitudinal section and isometric side view, respectively, of the dosing sleeve in the first example with a first limiting means.

Figure 3A:
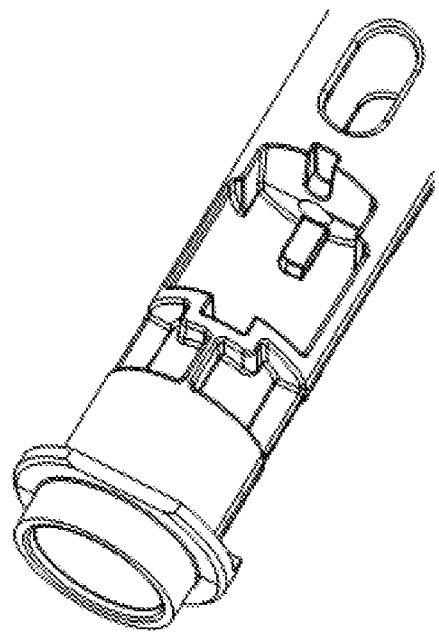
Figure 3B:
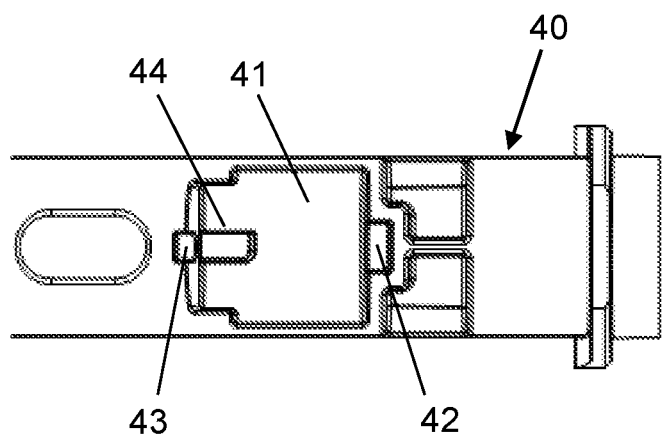
Figure 3C:
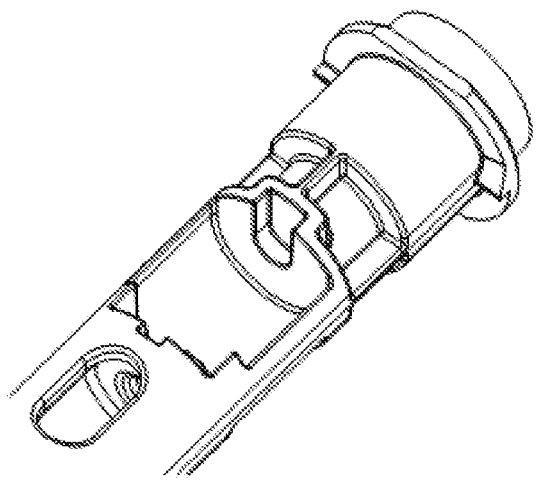

FIGS. 3a, 3b and 3c are a side and isometric views of the coupling sleeve in the first example.

Figure 4A:
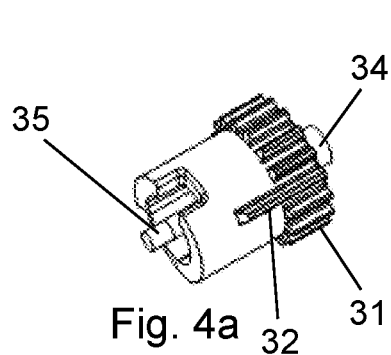
Figure 4B:
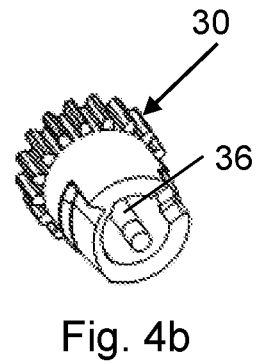
Figure 4C:
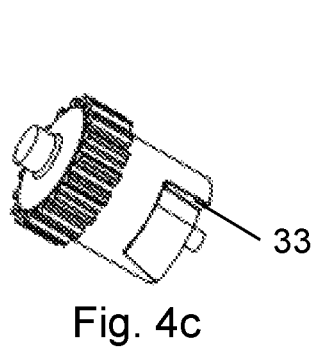

FIGS. 4a, 4b and 4c isometric side views of the second limiting means in the first example in the form of a stop wheel.

Figure 5A:
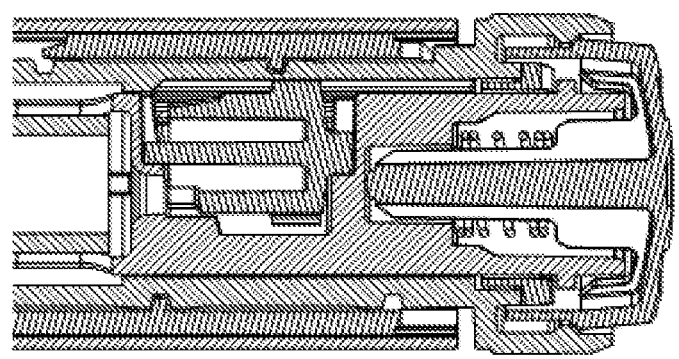
Figure 5B:
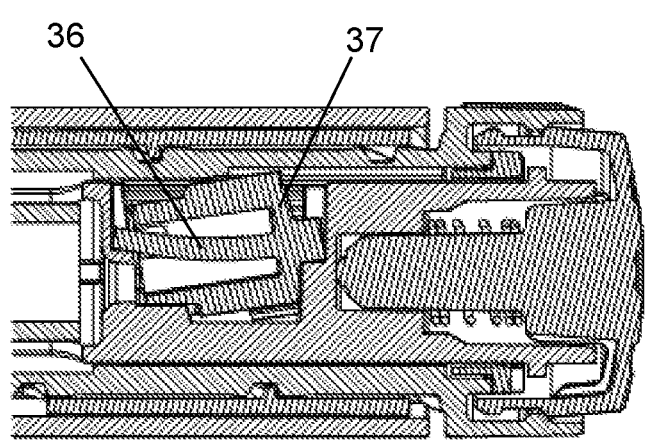

FIGS. 5a and 5b are longitudinal sections of the limiting mechanism in the first example in a normal position and a stop position, respectively.

Figure 6:
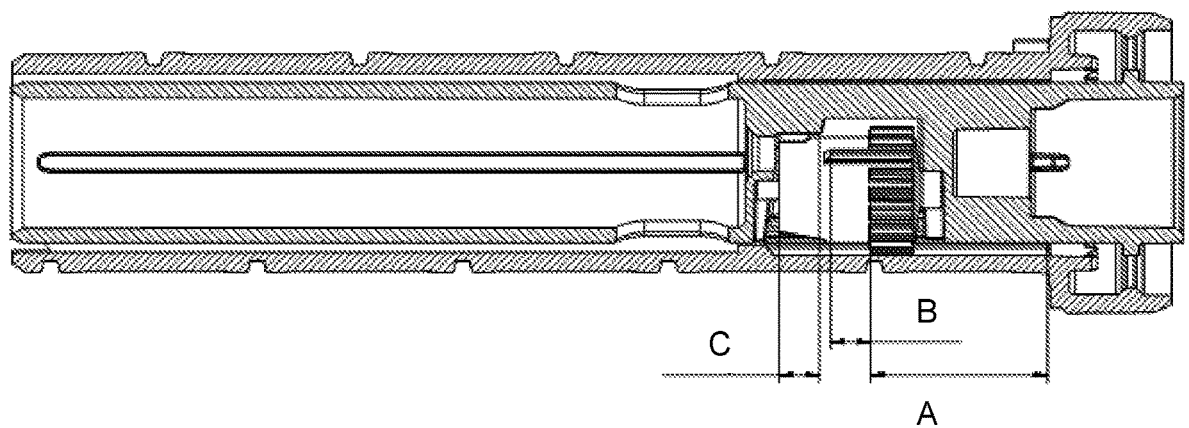

FIG. 6 is longitudinal section of the limiting mechanism in the first example with axial drive A, stop B and limit stop C zones.

Figure 7D:
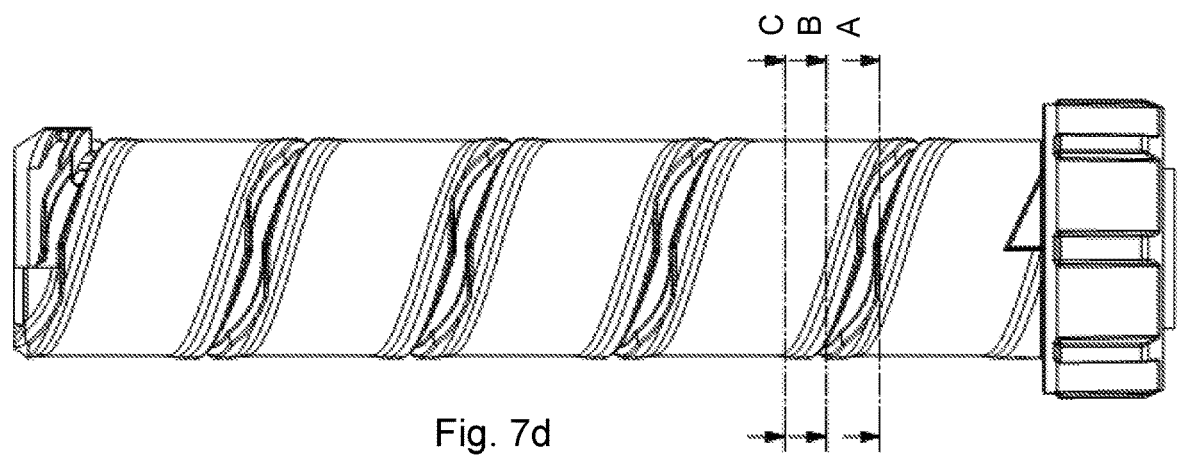
Figure 7C:
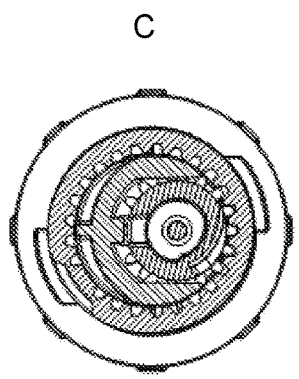
Figure 7B:
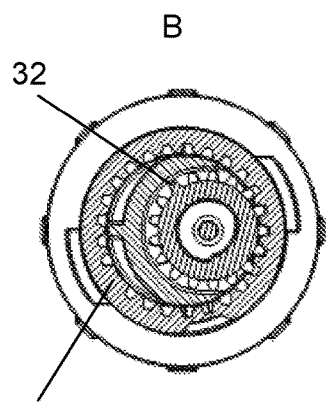
Figure 7A:
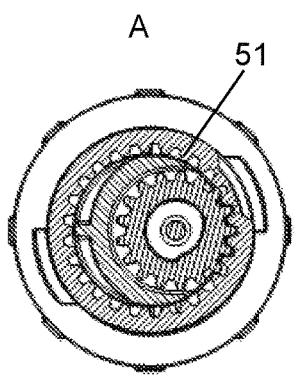

FIG. 7d is a side view of the limiting mechanism in the first example and FIGS. 7a-7c are cross sections thereof in axial drive A, stop B and limit stop C zones in a normal position.

Figure 8D:
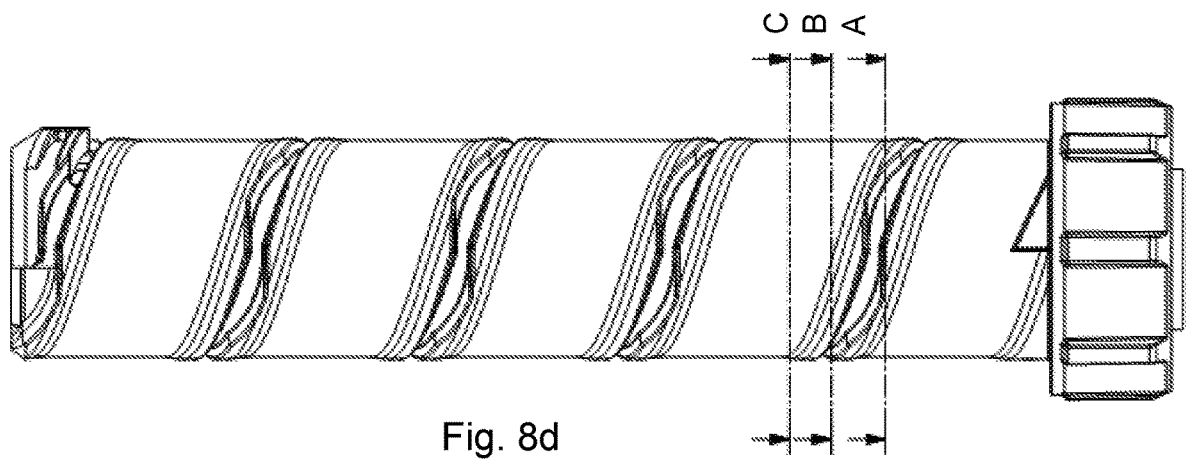
Figures 8A, 8B, 8C:
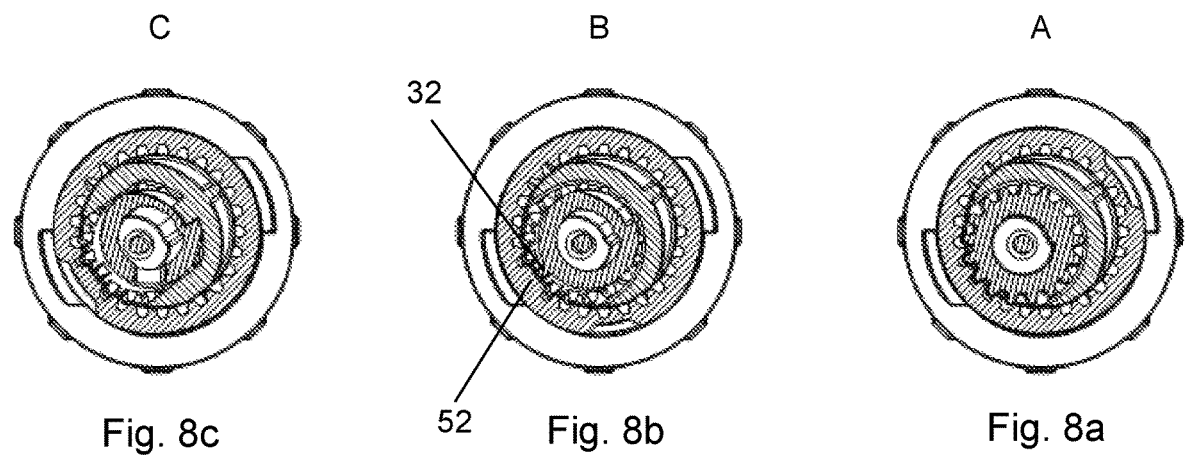

FIG. 8d is a side view of the limiting mechanism in the first example and FIGS. 8a-8c are cross sections in axial drive, stop and limit stop zones in a stop position.

Figure 9A:
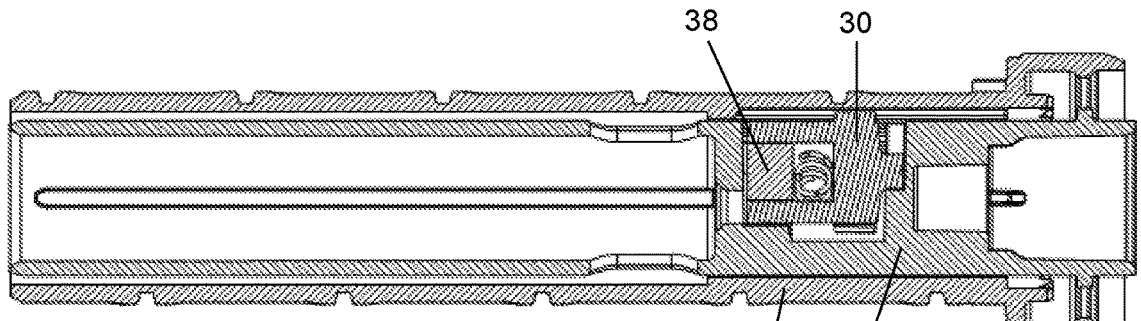
Figure 9B:
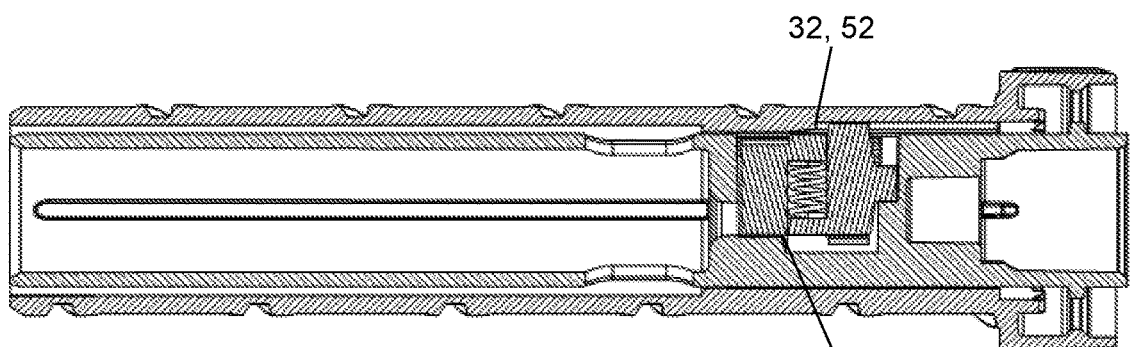
Figure 10A:
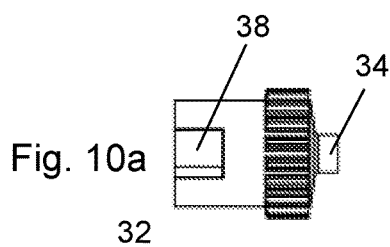
Figure 10B:
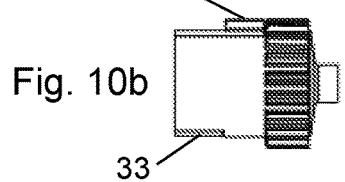
Figure 10C:
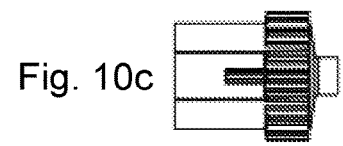
Figure 10D:
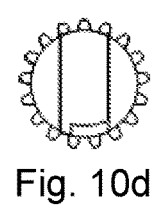
Figure 10E:
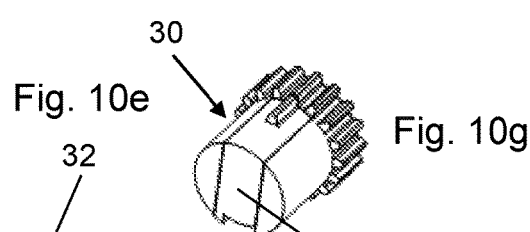
Figure 10F:
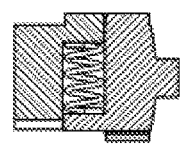
Figure 10G:
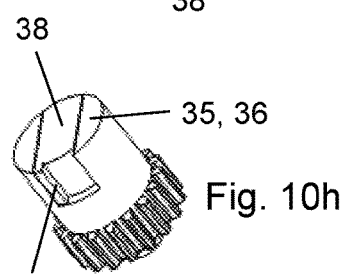
Figure 10H:
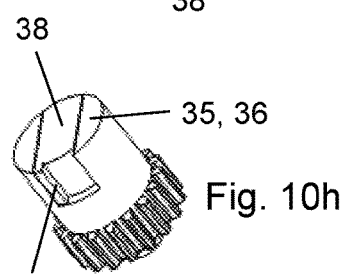

FIGS. 9a and 9b are longitudinal sections of the limiting mechanism in a second comparative prior art example in a normal position and a stop position, respectively.

FIGS. 10a-10h are side views and cross sections and two isometric views of the second limiting means in the second example in the form of a stop wheel with a transversely movable second limit stop means and a spring means.

Figure 11A:
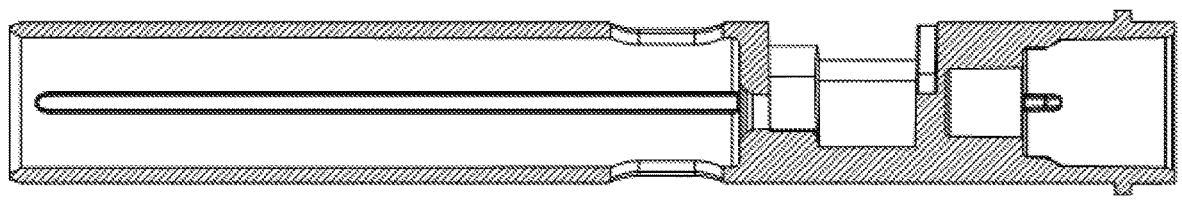
Figure 11B:
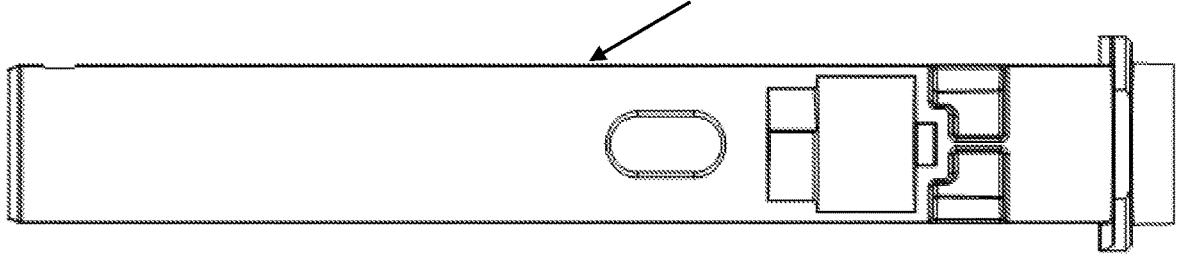

FIGS. 11a and 11b are a longitudinal section and a side view of the coupling sleeve in the second example, respectively.

Figure 12A:
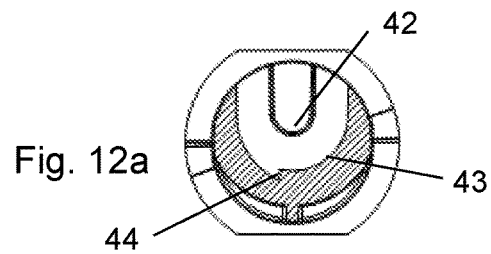
Figure 12B:
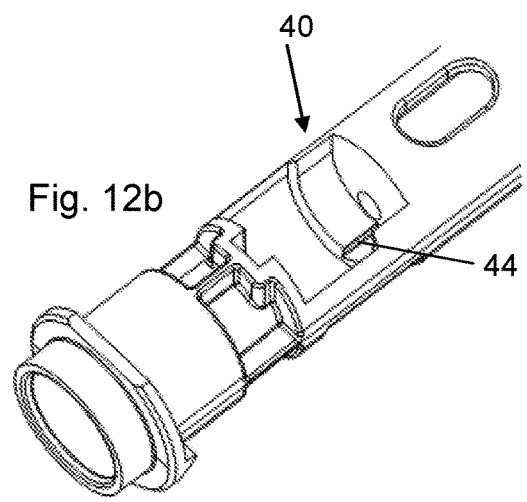

FIGS. 12a and 12b are a cross section and a side view of the coupling sleeve in the second example with a first limit stop means.

FIGS. 13a-1&2, 13b-1&2 and 13c-1&2 are pairs of cross section views of the limiting means in the second example in axial drive, stop and limit stop zones, each pair showing the means in a normal position and a stop position.

Figure 14A:
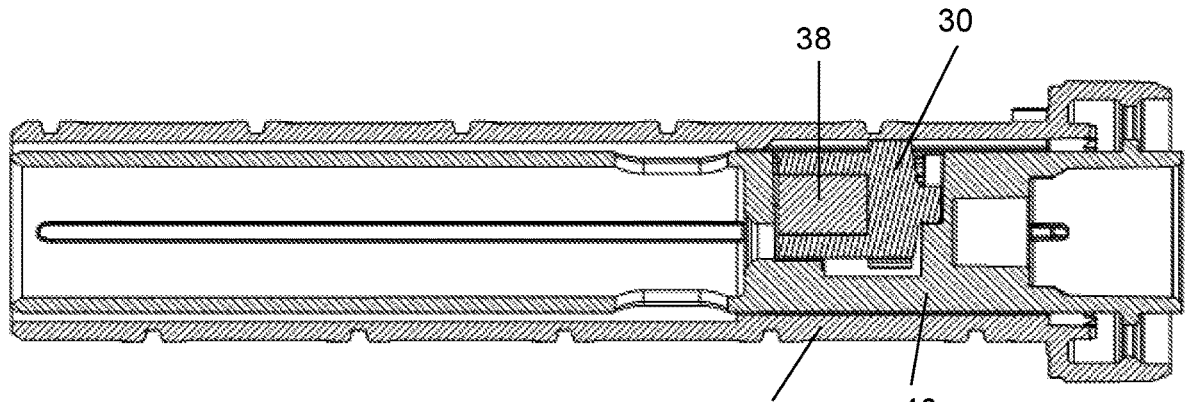
Figure 14B:
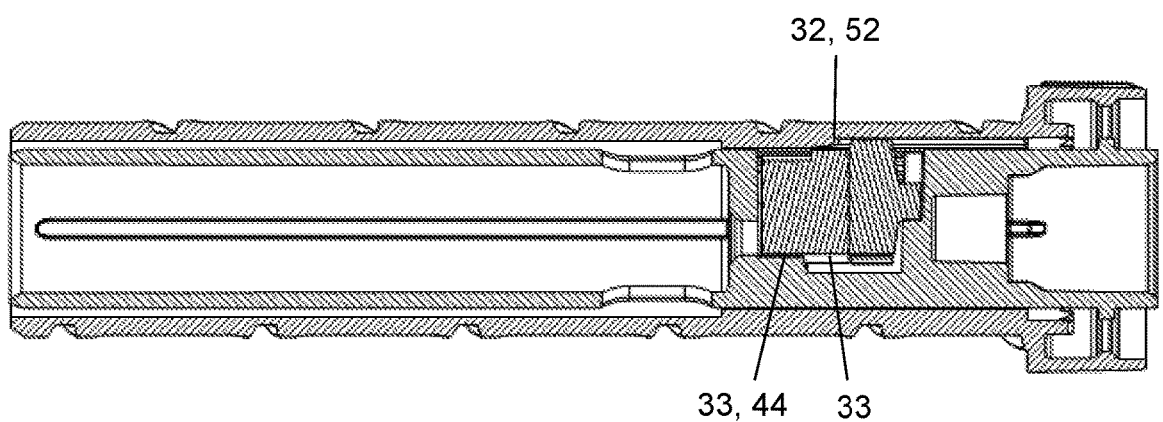
Figure 15A:
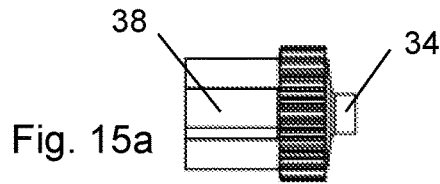
Figure 15B:
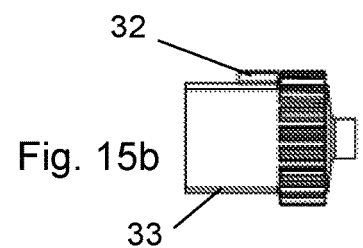
Figure 15C:
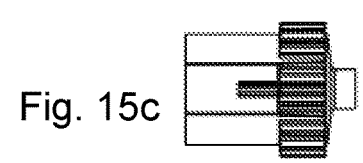
Figure 15D:
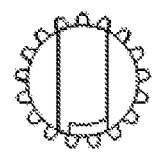
Figure 15E:
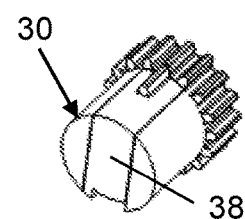
Figure 15F:
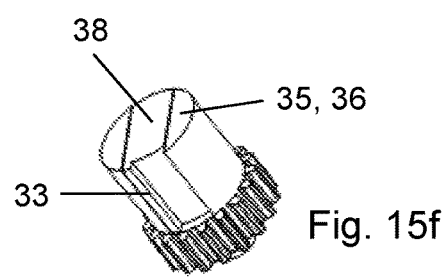

FIGS. 14a,14b are longitudinal sections of the limiting mechanism in a third comparative prior art example in a normal position and a stop position, respectively.

FIGS. 15a-15f are front views and cross sections and two isometric views of the second limiting means in the third example, in the form of a stop wheel with a transversely movable gearing means-guided second limit stop means.

Figure 16A:
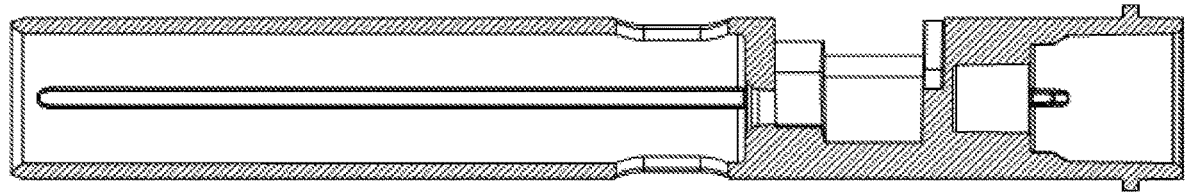
Figure 16B:
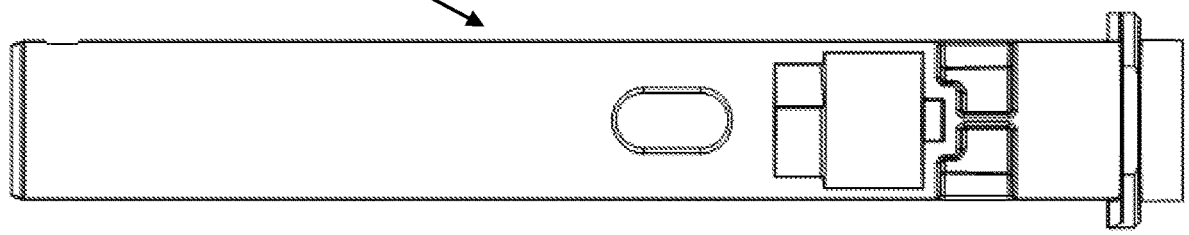

FIGS. 16a and 16b are a longitudinal section and side view of the coupling sleeve in the third example, respectively.

Figure 17A:
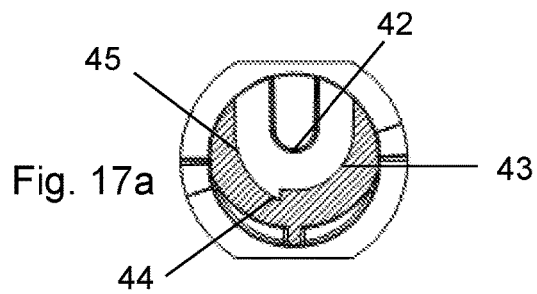
Figure 17B:
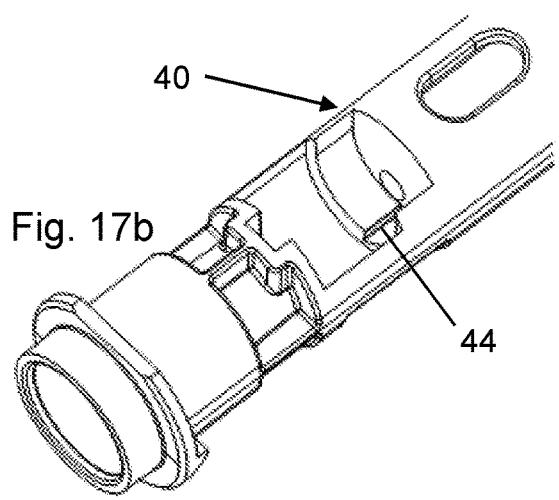
Figures 1, 18C:
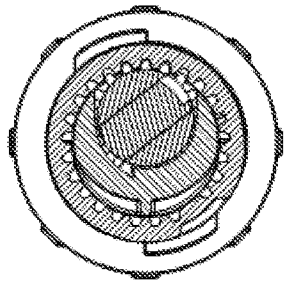
Figures 1, 18B:
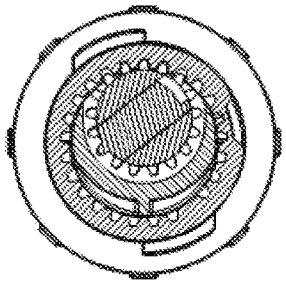
Figures 1, 18A:
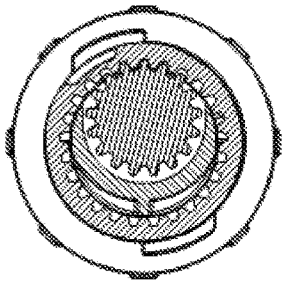
Figures 2, 18C:
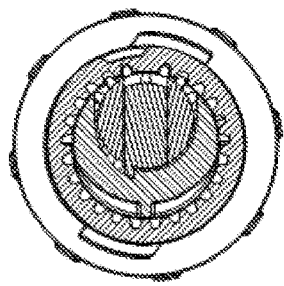
Figures 2, 18B:
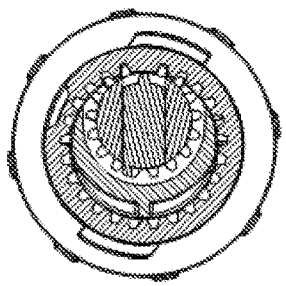
Figures 2, 18A:
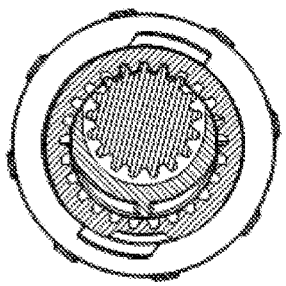

FIGS. 17a and 17b are a cross section and an isometric side view of the coupling sleeve in the third example using a limiting mechanism.

FIGS. 18a-1&2, 18b-1&2 and 18c-1&2 are pairs of cross section views of the limiting mechanism in the third example in axial drive, stop and limit stop zones, each pair showing the mechanism in a normal position and a stop position.

Figure 19A:
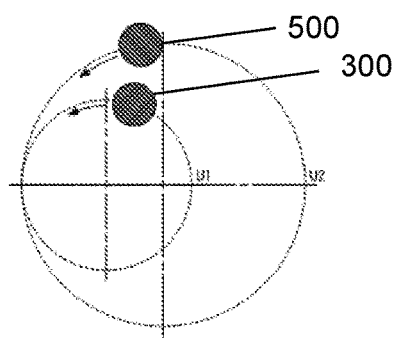
Figure 19B:
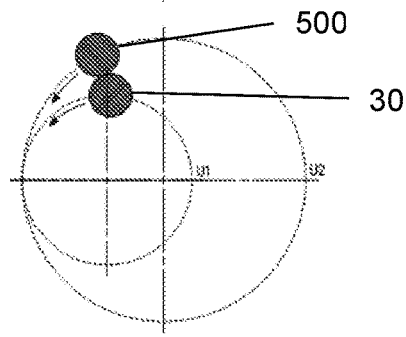

FIGS. 19a, 19b show schematically a motion and a stop path arrangement of the first through third examples.

Figure 20A:
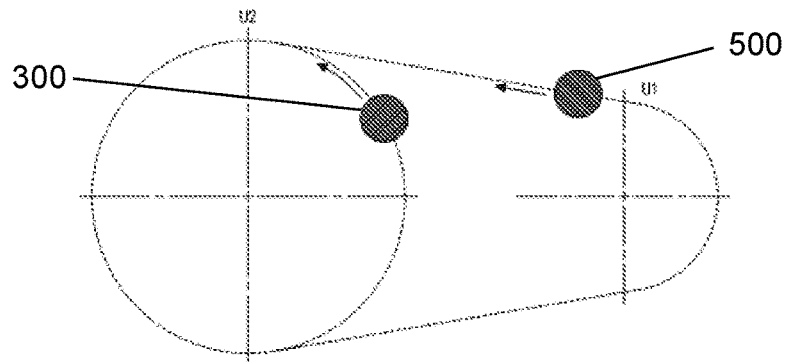
Figure 20B:
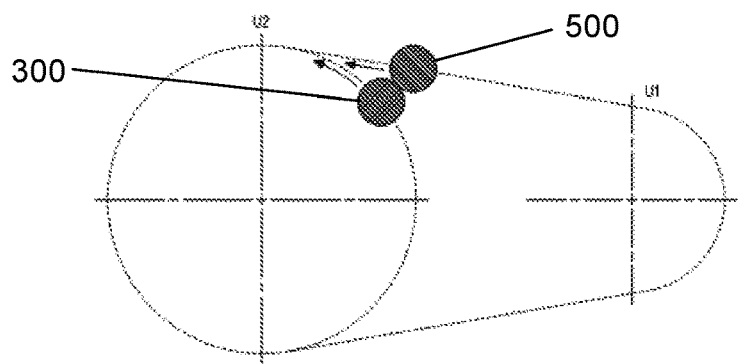

FIGS. 20a, 20b show schematically a motion and a stop path arrangement of a fourth comparative example.

Figure 21A:
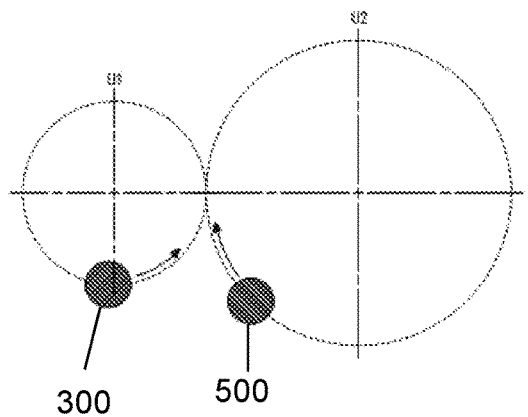
Figure 21B:
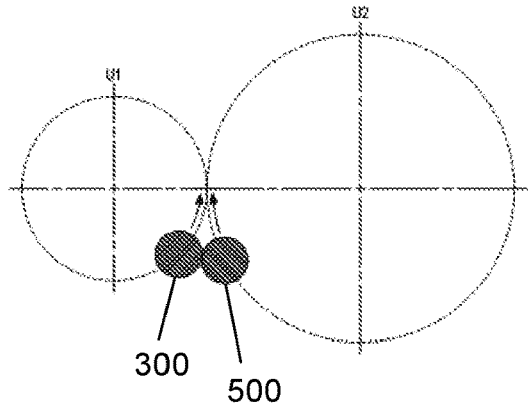

FIGS. 21a, 21b show schematically a motion and a stop path arrangement of a fifth comparative example.

Figure 22A:
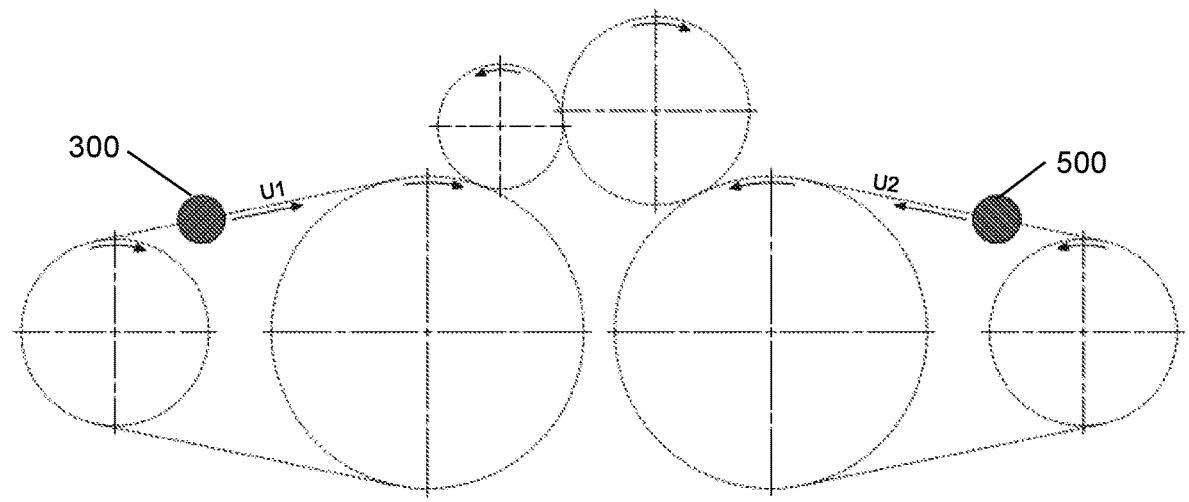
Figure 22B:
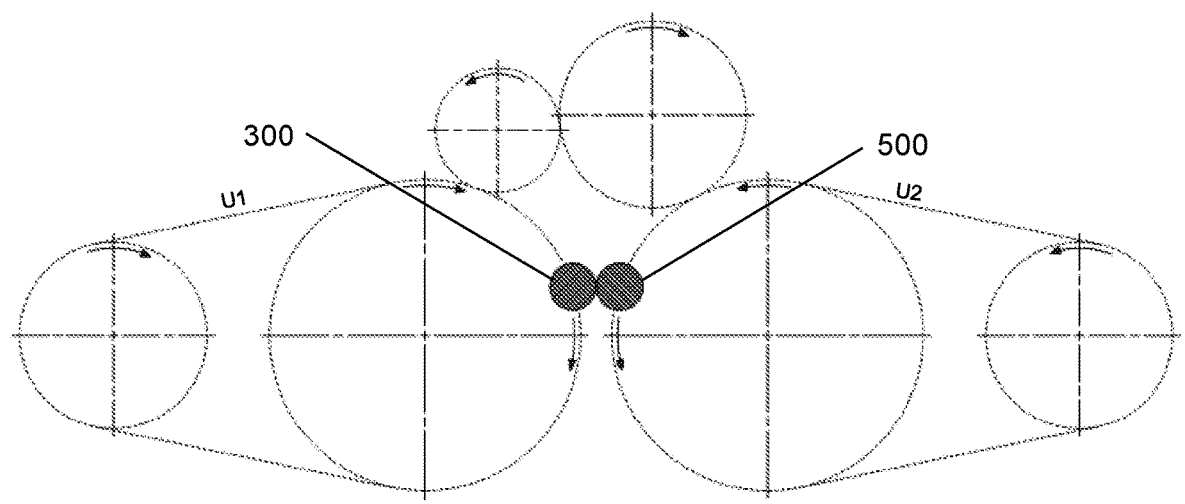
Figure 23A:
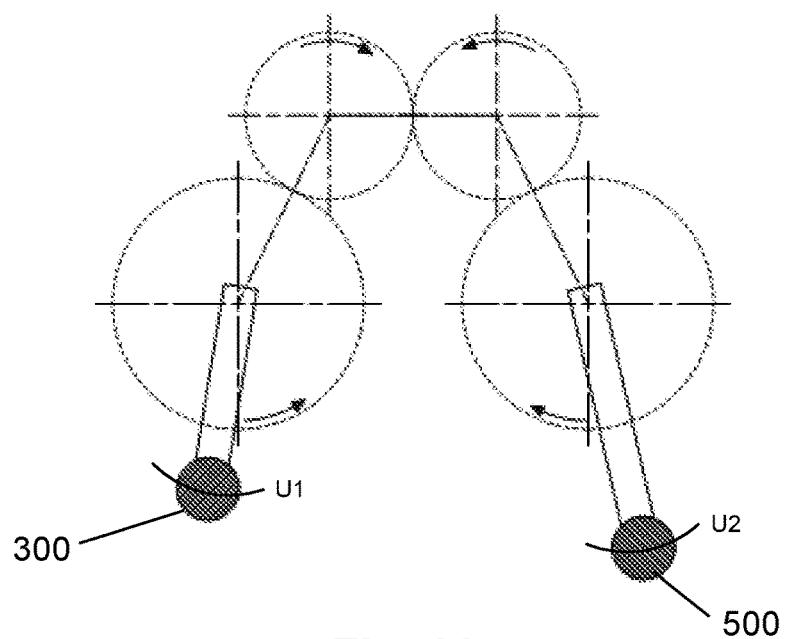
Figure 23B:
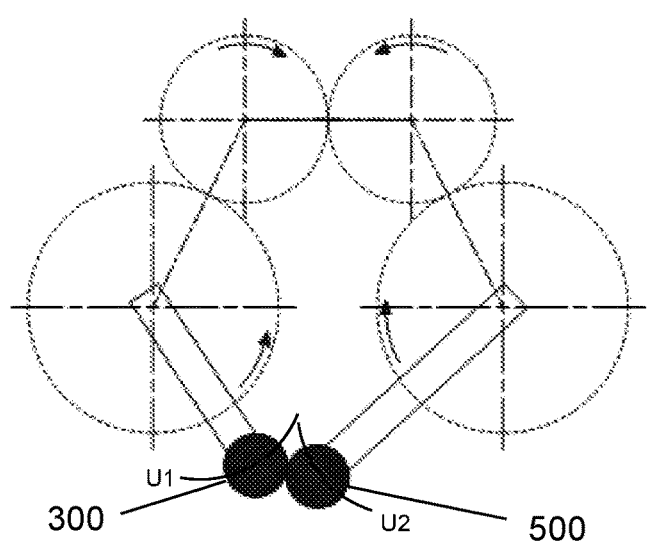

FIGS. 22a, 22b show schematically a motion and a stop path arrangement of a sixth comparative example FIGS. 23a, 23b show schematically a motion and a stop path arrangement of a seventh comparative example.

FIG. 24 shows an administration device with the dosing device according to the present disclosure, initial state, no dose set or delivered. Lines a-a, b-b and c-c define the location of cross sections that appear in the views of FIGS. 25a-25C.

FIGS. 25a, 25b and 25c show cross section through Zones A, B and C (per FIG. 24) of the device in the initial state.

Figure 26:
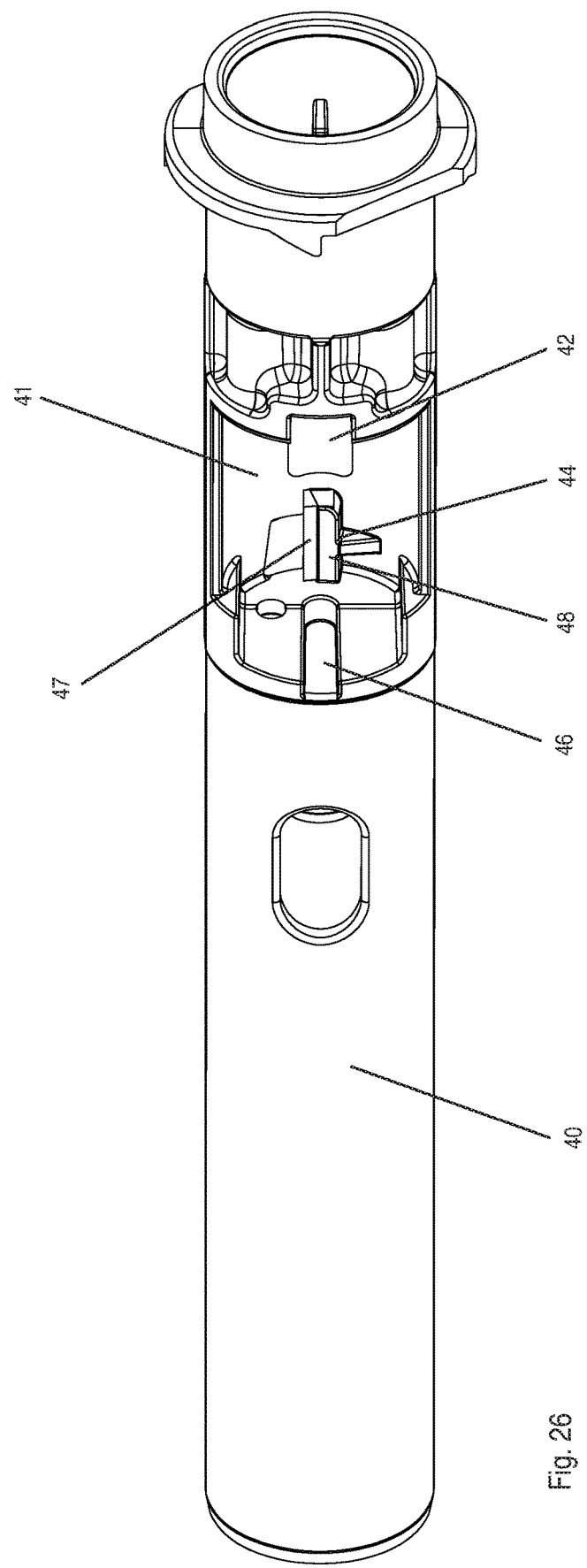

FIG. 26 shows a: clutch for the dosing device according to the present disclosure.

Figure 27:
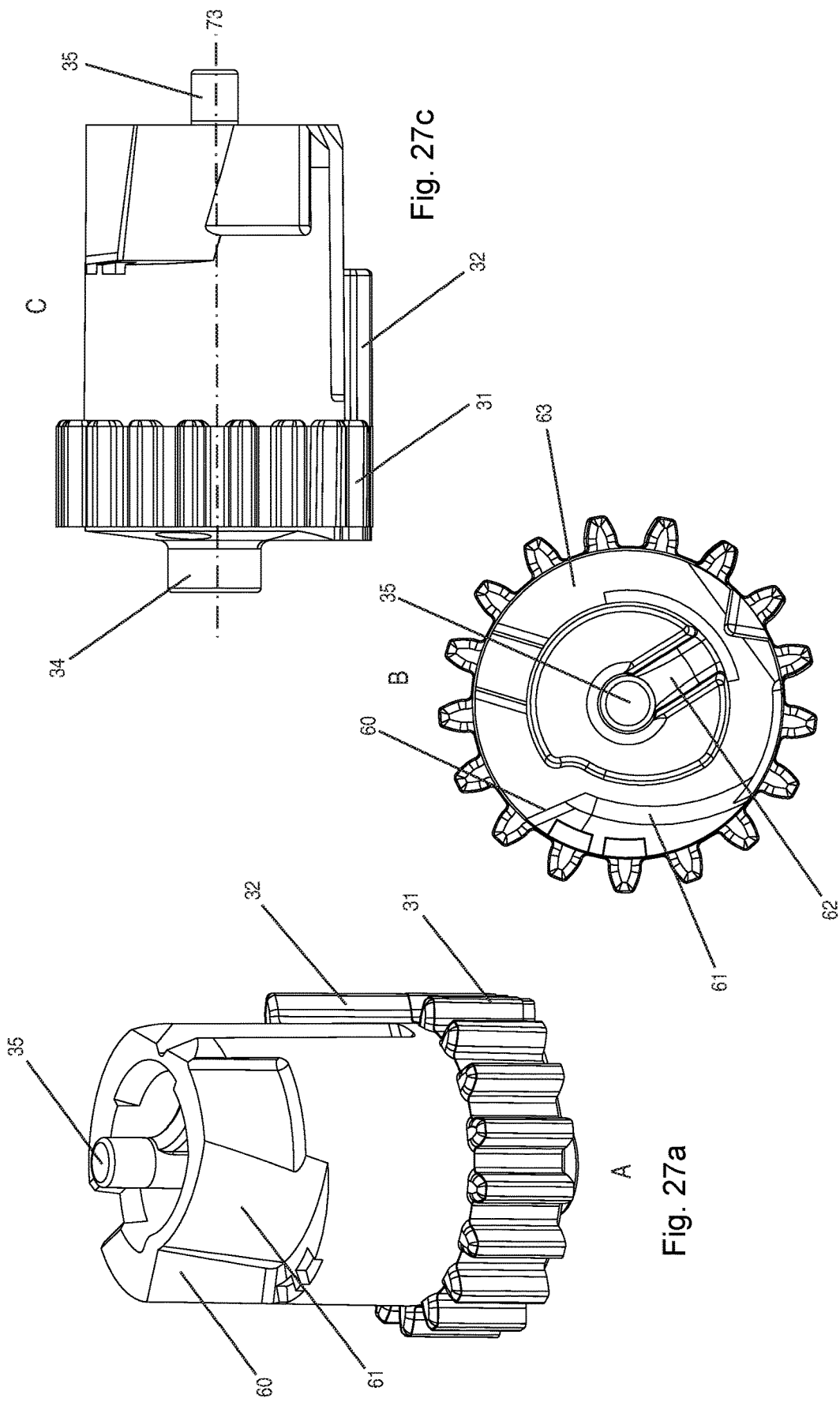

FIGS. 27a, 27b, and 27c show orthogonal, cross-section and side views of a stop wheel for the dosing device according to the present disclosure.

Figure 28:
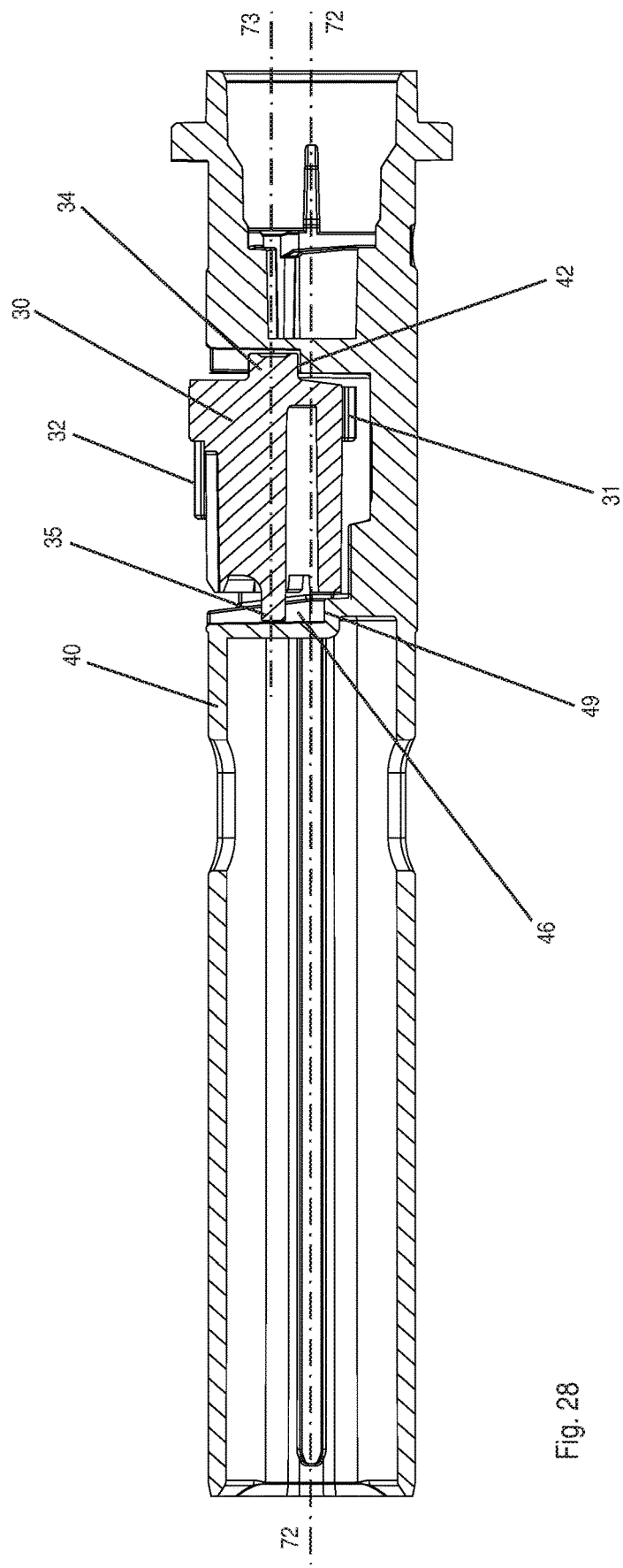

FIG. 28 shows assembly of clutch and stop wheel, with the stop wheel in the non-tilted position whereby the first and second longitudinal axes are parallel and off-set to each other.

FIG. 29 shows a stop wheel in the stop last dose position, wherein the stop wheel is tilted and the piston rod has advanced to the end of the cartridge. Lines a-a, b-b and c-c define the location of cross sections that appear in the views of FIGS. 30a-30C.

FIGS. 30a, 30b and 30c show cross section views through drive zone A, stop zone B, and limit stop zone C when the stop wheel is in the tilted last dose position of FIG. 29; wherein abutment of the stop wedge 52 and stop rib 32 in Zone B tilts the stop wheel and prevents the first gear guidance (60, 47) shifting the stop wheel back to the non-tilted position.

FIG. 31 shows a stop wheel accidentally tilted during use when the piston rod has not advanced towards the end of the cartridge. Lines a-a, b-b and c-c define the location of cross sections that appear in the views of FIGS. 32a-32c.

FIGS. 32a, 32b and 32c show a stop wheel accidentally tilted and the second gear guidance (61, 48) is not in abutment yet in Zone C while the stop wheel can be driven in Zone A during dial down dosing.

Figure 33:
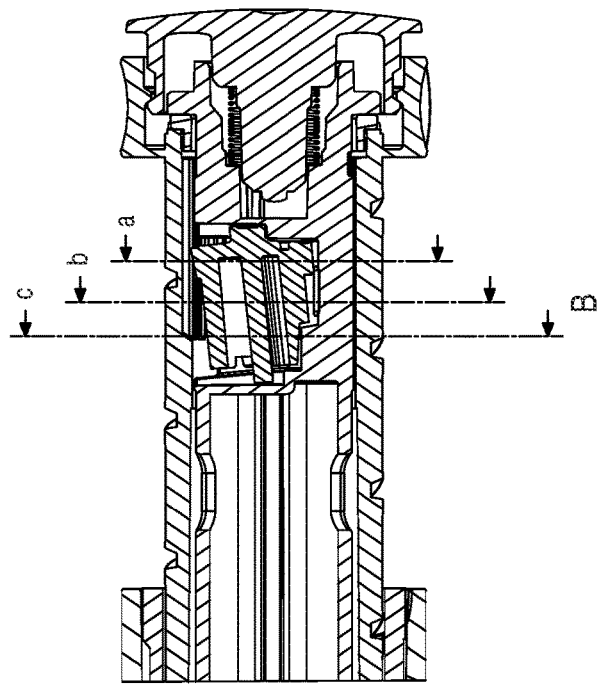

FIG. 33 shows a stop wheel partially returned to the non-tilted position during dial down dosing. Lines a-a, b-b and c-c define the location of cross sections that appear in the views of FIGS. 34a-34C.

Figure 34A:
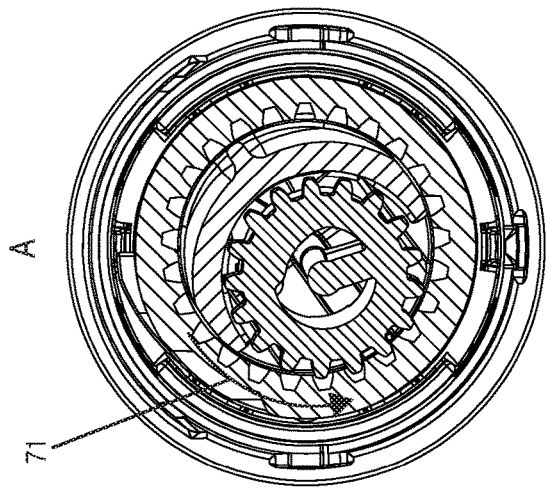
Figure 34B:
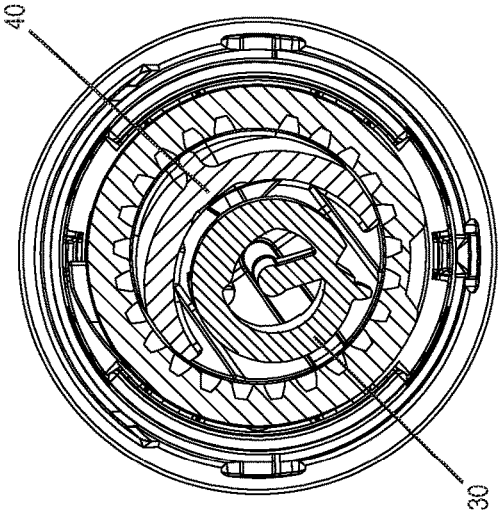
Figure 34C:
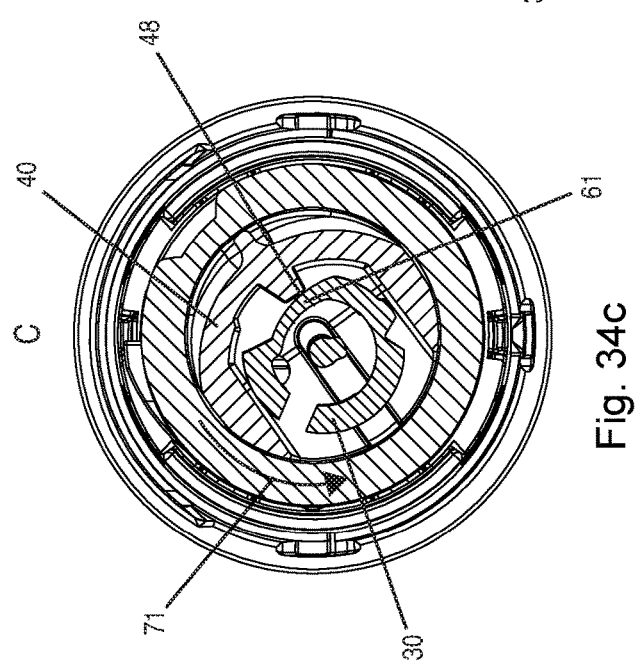

FIGS. 34a, 34b and 34c are cross sections showing the abutment of the second gear guidance (48, 61) in Zones A, B and C (from FIG. 33) during dial down dosing.

Figure 35:
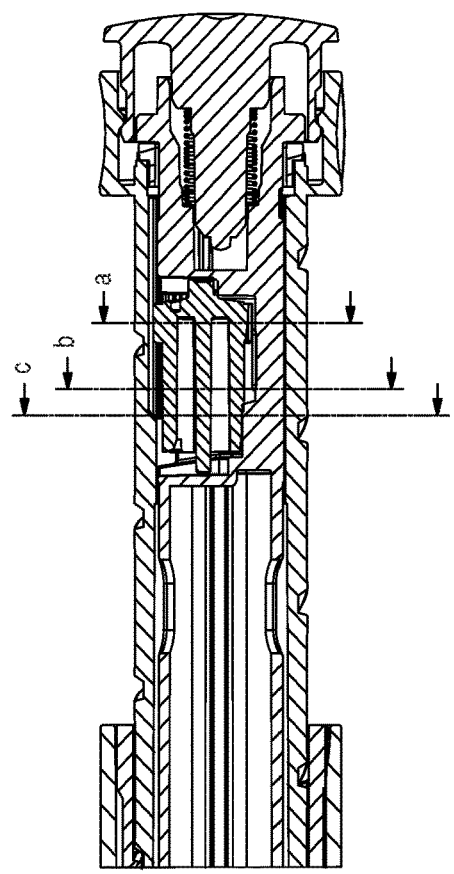

FIG. 35 shows a stop wheel returned to the non-tilted position during dial down dosing by the second gear guidance. Lines a-a, b-b and c-c define the location of cross sections that appear in the views of FIGS. 36a-36C.

Figure 36A:
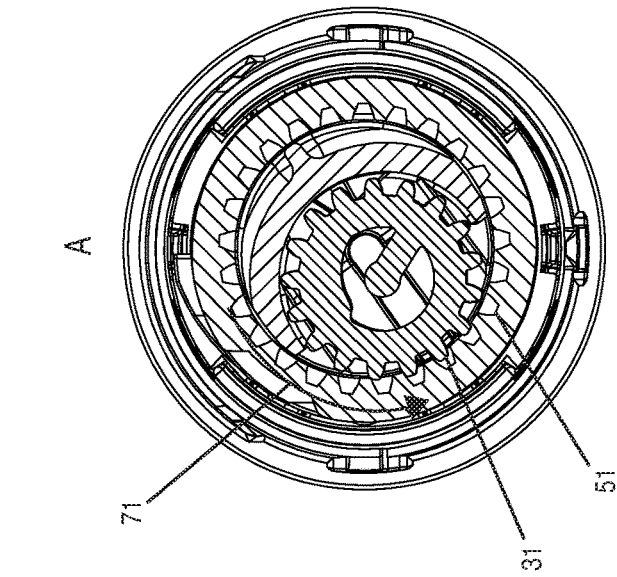
Figure 36B:
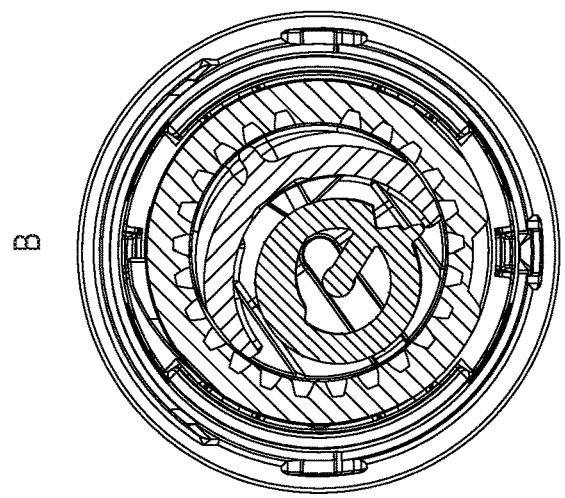
Figure 36C:
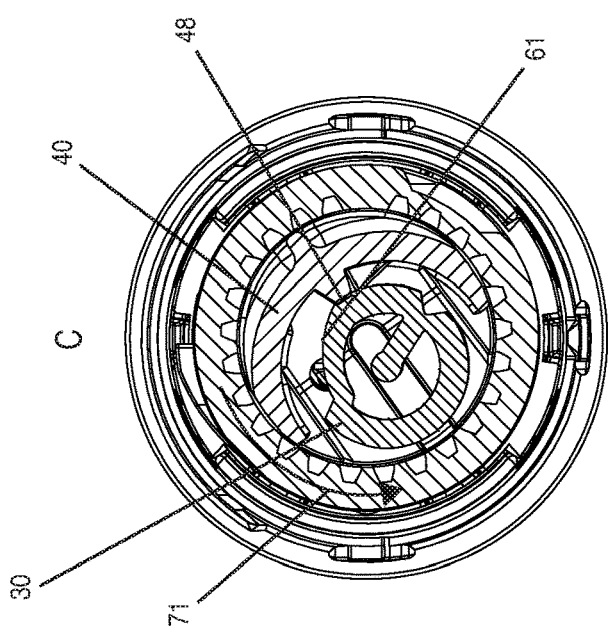

FIGS. 36a, 36b and 36c show cross sections through zones A, B, C during dial down dosing showing the second gear guidance shifting the stop wheel back to the non-tilted position.

Figure 37A:
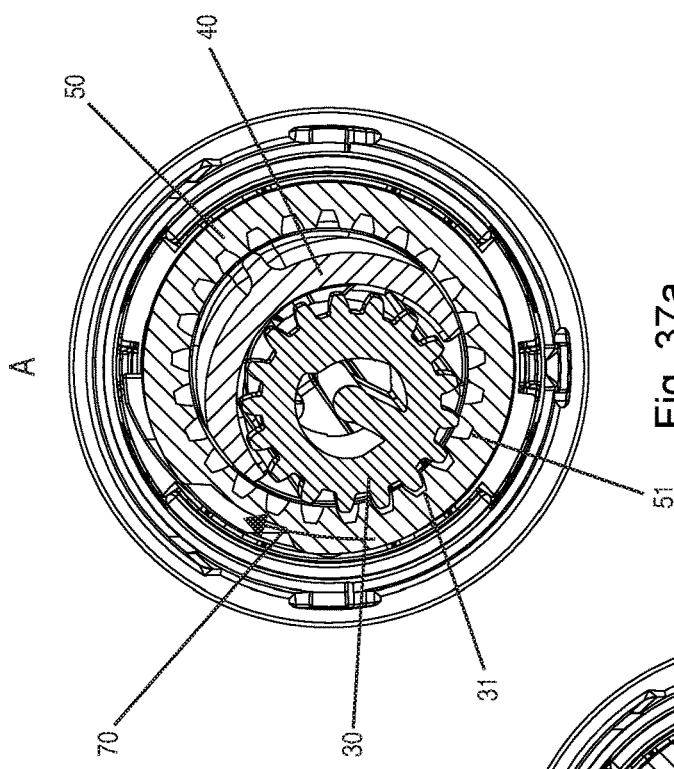
Figure 37B:
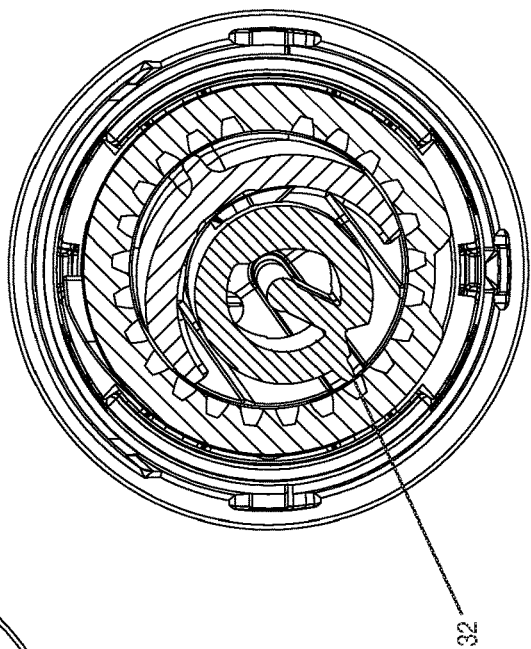
Figure 37C:
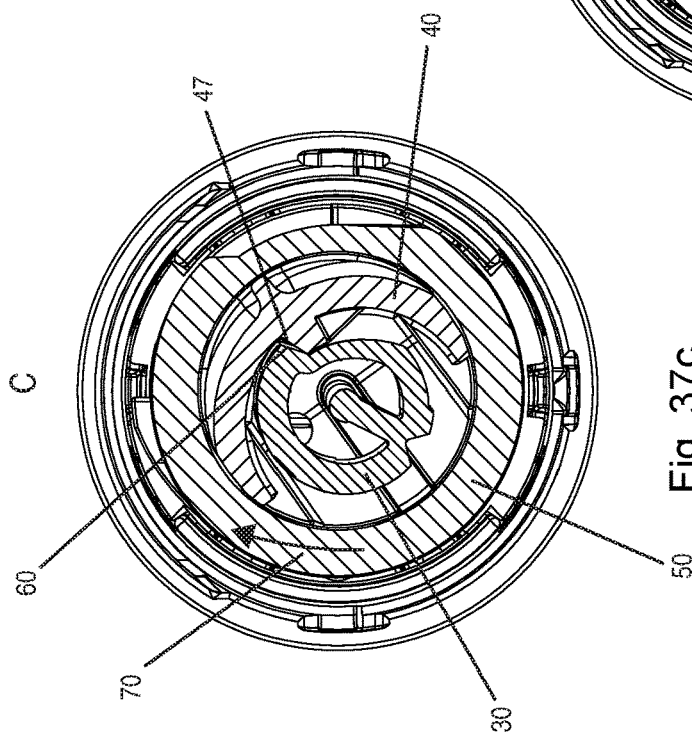

FIGS. 37a, 37b and 37c show cross sections through zones A, B, C when the stop wheel accidentally is in the tilted position; in drive zone A, the stop wheel is rotated such that the first gear guidance (60, 47) gets into abutment during dial up dosing.

Figure 38A:
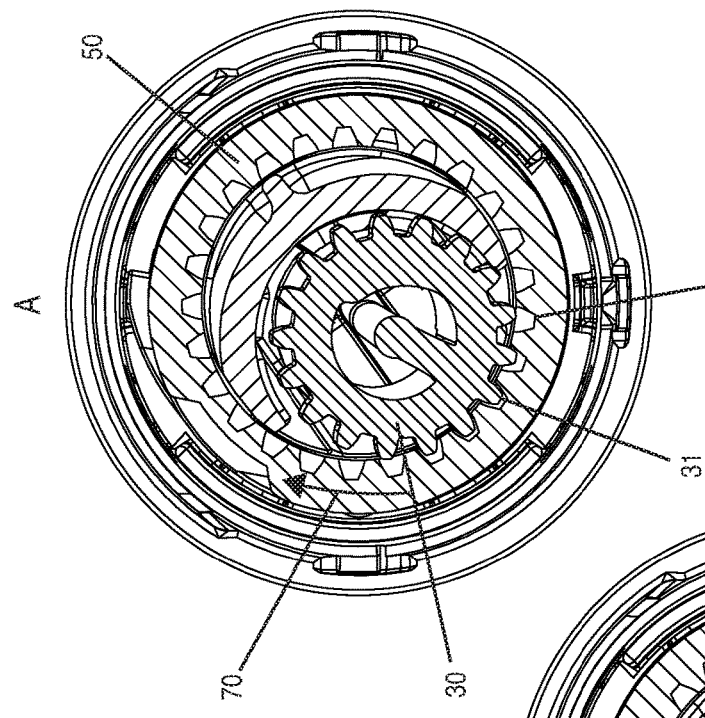
Figure 38B:
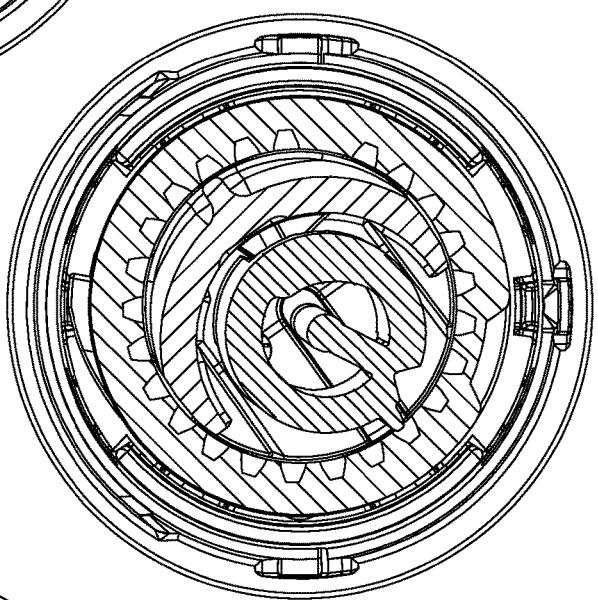
Figure 38C:
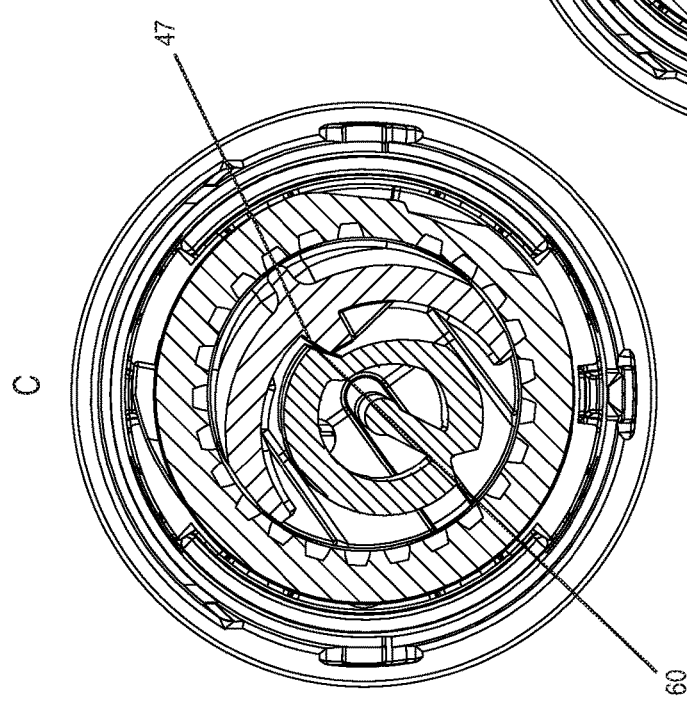

FIGS. 38a, 38b and 38c show cross sections through zones A, B, C, with partial return of the stop wheel due to the first gear guidance (60,47) during dial up dosing.

FIGS. 39a, 39b and 39c show cross sections through zones A, B, C, with full return of the stop wheel due to the first gear guidance (60,47) during dial up dosing.

FIG. 1 shows an exploded view of the individual parts of a first comparative example of an injection device according to the prior art per the EP2814547A1 application. FIGS. 2a-b show a longitudinal section and a side view of the dosing sleeve in the first example with the first limiting means. FIGS. 3a-b show side views of the coupling sleeve in the first example. FIGS. 4a-c show side views of the second limiting means in the first example in the form of a stop wheel. FIGS. 5a-b show longitudinal sections of the limiting mechanism in the first example in a normal position and a stop position. FIG. 6 shows a longitudinal section of the limiting mechanism in the first example with axial drive A, stop B and C limit stop zones. FIGS. 7a-d show a side view of the limiting mechanism in the first example and cross sections in the axial drive, stop and limit stop zones in a normal position. FIG. 8a-d show a side view of the limiting mechanism in the first embodiment and cross sections in the axial drive, stop and limit stop zones in a stop position.

The first comparative example is designed as a so-called single-use pen. That is to say, the ejection device is issued to the user fully assembled, i.e., with product to be administered. Before use, the user need only expel the air from the injection device, also known as priming. The typical course of the injection process may be as follows: the user removes the protective cap 1 from the injection device and mounts an injection needle (not shown) on the needle holder 2a. Now the dosage can be adjusted via the rotary knob 11 a. For this purpose, the rotary knob 11a is turned so that the dosing sleeve 50 is screwed out of the injection device. The dosing sleeve 50 is screwed out of the injection device until the desired dosage is displayed in the window of the threaded sleeve 9. If an excessively high dosage is inadvertently set, the dosage can be corrected by turning the rotary knob in the opposite direction, whereby the dosing sleeve 50 is screwed back into the housing. The dosing device limits the maximum adjustable dosage to a predetermined value. If there is an attempt to screw the dosing sleeve out of the housing past this value, a radial limit stop on the dosing sleeve 50 and a counter-limit stop on the threaded sleeve 9 prevent further rotation by mutual interaction.

During the dosing and correction movements, the dosing sleeve 50 rotates relative to the coupling sleeve 40. The coupling sleeve 40 is held rotationally fixedly in a form fit or friction fit against the housing 5 by a reverse rotation lock (e.g., applied to the threaded nut 7 and housing 5), for example by means of latch and snapping means. If the desired dosage has been set, the injection needle can be inserted at the intended position on the body of the user. Then the user pushes the ejection button 14 in the distal axial direction and thus blocks a relative rotation between the coupling sleeve 40 and the dosing sleeve 50. In case of further pressure in the distal axial direction, the dosing sleeve begins to move back into the housing in a screwing motion. Because of the established rotational lock between the dosing sleeve and the coupling sleeve, the coupling sleeve 40 carries out the same movement as the dosing sleeve 50. Because the coupling sleeve 40 is permanently rotationally locked to the axially stationary threaded nut 7, the rotational movement of the dosing sleeve 50 is transmitted to the threaded nut 7. No axial forces are transmitted to the threaded nut 7, because the coupling sleeve 40 is mounted axially movably on the threaded nut 7. Thus the rotating threaded nut 7 produces an axial movement of the threaded rod 8 in the distal direction, wherein the latter is guided axially and locked rotationally in the housing 5. The flange 4 acts on the plug of the cartridge and pushes it, corresponding to the displacement of the threaded rod 8 in the distal direction as well, wherein the previously set dosage can be ejected or administered. At the end of the administration, when the dosing sleeve has been completely screwed back into the housing, radial stops on the dosing sleeve 50 and the threaded sleeve 9 prevent further ejection and over-rotation of the dosing device.

The limiting device according to the disclosure ensures that the most recently set dosage can be completely ejected or injected.

For this purpose, the dosing sleeve 50 with outer wall 50a has on its inner wall coaxially applied toothing 51, which can extend axially over the three axial sections, drive zone A, stop zone B and limit stop zone C. Circumferential toothing is formed at least in the drive zone A. A first stop means is formed as a stop wedge 52 in the axial extension of a tooth interstice of the circumferential toothing 51 in the stop zone B. As described above, the coupling sleeve 40 is inserted coaxially into the dosing sleeve 50. Preferably, the coupling sleeve 40 has a lateral cutout 41, which extends at least in certain sections across the three sections, drive zone A, stop zone B and limit stop zone C, and in which the stop wheel 30 is inserted. The rotational shaft 36 of the wheel, connected by spoke means 37 to the wheel, is rotatably received at its proximal shaft end 34 in the proximal bearing 42, and at its distal shaft end 35 in the distal bearing 43 of the coupling sleeve 40. At least in one area of the drive zone A, circumferential toothing 31, with 17 teeth, for example, which mesh with the circumferential toothing 51, with 25 teeth, for example, on the dosing sleeve 50, is formed on the stop wheel 30. The transmission formed in this manner sets the stop wheel 30 into rotation whenever the dosing sleeve 50 and the coupling sleeve 40 rotate relative to one another about their common axis L. The rotational shaft 36 of the stop wheel 30 is offset parallel to this axis L. A second stop means is formed as a stop rib 32 in the axial extension of the tooth in the circumferential toothing 31, at least in the stop zone B. In the limit stop zone C, a first limit stop means is formed in the cutout 41 of the coupling sleeve 40 as a radially acting limit stop 44, which can be brought into engagement with a second limit stop means constructed as a radially acting counter-limit stop 33 in the limit stop zone C on the stop wheel 30. This engagement takes place by pivoting the stop wheel 30 out of a normal position into a stop position against the elastic force of its rotational shaft 36 and/or the elastic force of its spoke means 37. The engagement prevents further rotation of the stop wheel 30 in the dosage-increasing direction. Because a rotation of the coupling sleeve 40 relative to the housing 5 in the dosage-increasing direction is blocked by the reverse rotation lock, the dosing sleeve 50 can also not be rotated further in the dosage-increasing direction by the interlinkage formed by the toothing 31 and the toothing 51. Conversely, the engagement and this blocking due to the restoring force of the rotational shaft are released as soon as the stop rib 32 detaches from the stop wedge 52 during a rotation of the stop wheel 30 in the dosage-reducing direction and the pivoted stop wheel can move back into its normal position. The stop wheel 30 is pivoted only when the stop rib 32 strikes the stop wedge 52. With 25 teeth for toothing 51 and 17 teeth for toothing 31 for example, and with a maximally selected starting position, this occurs after 25 times 17=425 tooth pitches, which corresponds to one period. The stop wheel 30 turns 25 times and the dosing sleeve 50 turns 17 times in this example until the stop rib 32 strikes the stop wedge 52 and the resulting transverse force brings the first and second limit stop means into engagement, as already described. By suitable selection of the initial position of the stop wheel 30, the dosage limitation can be programmed to any desired number and fractions of tooth pitches or rotations inside the period, without structural changes having to be made to the design. For example, one tooth pitch can correspond to one insulin unit IU. and the stop wheel can be initially inserted at the point corresponding to 125 tooth pitches [per period?], so that limitation occurs after a total of 300 preselected or ejected IU.

FIGS. 9-13 show a second comparative prior art example of an environment in which the device according to the disclosure may be installed, a further example of an injection device similar to FIG. 1. FIGS. 9a and b show longitudinal sections of the limiting mechanism of the second example in a normal position and in a stop position. FIG. 10 shows side views and cross sections of the second limiting means in the second example in the form of a stop wheel with a transversely movable second limit stop means and spring return. FIG. 11 shows a side view and a longitudinal section of the coupling sleeve in the second example. FIG. 12 shows a side view and a cross section of the coupling sleeve in the second example with a first limit stop means. FIG. 13 shows cross sections of the limiting mechanism in the second example in axial drive, stop and limit stop zones in a normal position and a stop position.

The application and function of the second example correspond to the first example apart from the following modifications made for the sake of example. The stop wheel 30 is designed with a rigid rotational shaft 36, the wheel and the shaft preferably being solidly integrated, and is rotatably received at the proximal shaft end 34 in the proximal bearing 42 and at its distal shaft end 35 in the distal bearing 43 of the coupling sleeve 40. In the area of the stop zone B and the limit stop zone C, a transverse guidance groove with inserted slider 38 is provided in the rotational shaft 36 or in the stop wheel 30. In the slider 38 or in the rotational shaft 36, a space is opened in the interior in the area of the stop zone, in which a spring means 39, preferably a compression spring in the form of a helical spring, is seated. This spring means holds the slider 38 in its transversal normal position. In this position, the stop rib 32 on a face of the slider 38 can mesh with toothing 51 optionally formed in the area of the stop zone, so long as the stop rib 32 does not strike the stop wedge 52. If that is the case, the slider is shifted transversely to the rotational shaft against the elastic force of the spring means 39 into a stop position. The counter-limit stop 33 formed on the side face of the slider 38 opposite the stop rib 32 as a second limit stop means is thereby brought into engagement with the limit stop 44 applied as a first limit stop means to the coupling sleeve 40. The engagement prevents further rotation of the stop wheel 30 in the dosage-increasing direction. Conversely, this engagement is released by the restoring force of the spring means 39 as soon as the stop rib 32 detaches from the stop wedge 52 during a rotation of the stop wheel 30 in the dosage-reducing direction and the slider 38 can move back into its normal position due to the force of the spring means 39.

FIGS. 14-18 show a third comparative prior art example of an environment in which the device according to the disclosure may be installed, a further example of an injection device similar to FIG. 1. FIGS. 14a and b show longitudinal sections of the limiting mechanism of the third example in a normal position and in a stop position. FIG. 15 shows front views of the second limiting means in the third example in the form of a stop wheel with a transversely movable second limit stop means and gearing means return. FIG. 16 shows a side view and a longitudinal section of the coupling sleeve in the third example. FIG. 17 shows a side view and a cross section of the coupling sleeve in the third example with a first limiting means and a gear cam. FIG. 18 shows cross sections of the limiting mechanism in the third example in axial drive, stop and limit stop zones in a normal position and a stop position.

The application and function of the third example correspond to the first example apart from the following modifications made for the sake of example. The stop wheel 30 is designed with a rigid rotational shaft 36, the wheel and the shaft preferably being solidly integrated, and is rotatably received at the proximal shaft end 34 in the proximal bearing 42 and at its distal shaft end 35 in the distal bearing 43 of the coupling sleeve 40. In the area of the stop zone B and the limit stop zone C, a transverse guidance groove with inserted slider 38 retracted in its normal transversal position is provided in the rotational shaft 36 or in the stop wheel 30. In this normal position, the stop rib 32 on a face of the slider 38 can mesh with toothing 51 optionally formed in the area of the stop zone, so long as the stop rib 32 does not strike the stop wedge 52. If that is the case, the slider 38 is moved transversely to the rotational shaft against defined static and sliding frictional forces into its stop position. The counter-limit stop 33 formed on the side face of the slider 38 opposite the stop rib 32 as a second limit stop means is thereby brought into engagement with the limit stop 44 positioned as a first limit stop means on the coupling sleeve 40. The engagement prevents further rotation of the stop wheel 30 in the dosage-increasing direction. Conversely, this engagement is released in case of a rotation of the stop wheel 30 in the dosage-reducing direction. Then the stop rib 32 again detaches from the stop wedge 52, and the slider 38 is moved back into its normal position based on the transmission-like interaction of the counter-limit stop 33, on a side face of the slider 38 opposite from the stop rib 32, and the gear cam 45 in the coupling sleeve 40.

It is understood that the dosage limitation in examples according to the disclosure also functions if the first and second limit stop means in the previous examples are omitted and the blocking of the rotational movement takes place only by the striking of first and second stop means.

An additional blocking mechanism can also be provided in all examples. When the last possible quantity of product to be administered has been ejected, i.e., when the cartridge 3 has been completely emptied, the conveying device blocks further ejection rotation of the dosing sleeve 50. In that case, the end 8a (FIG. 1) of the thread on the threaded rod 8 strikes against the ribs of the inside thread of the threaded nut 7 and prevents any further axial movement of the threaded rod 8 relative to the threaded nut 7. Because the threaded rod 8 is rotationally locked with respect to the housing, no common rotation of the threaded nut 7 and the threaded rod 8 is possible. Consequently, the dosing sleeve 50 is prevented from screwing in farther, so long as the rotational lock between the coupling 40 and the dosing sleeve 50 is maintained. If a higher dosage was set than the amount of product that remains, then the non-administered remaining quantity can be read off through the window on the dosing sleeve 50 in the blocked state. This remaining quantity would then have to be injected in another administration process with a spare injection device. This inconvenience is generally avoided, however, by the limiting device according to the disclosure and the injection device shown as an example. That is to say, the end 8a of the thread on the threaded rod 8 contacts the ribs of the inside thread of the threaded nut 7 at the earliest when the dosing sleeve 50 has reached and displayed the remaining amount "0" and the cartridge is nominally empty.

In general, the previously presented examples of the disclosure can be viewed as representatives of an arrangement as shown in FIGS. 19a and 19b. The stop means 300, 500 in this case move at the same speed, operatively connected in a form-fit to one another, on circular paths U1, U2 of different sizes, the axis of the smaller circle U1 lying inside the larger circle U2.

Representatives of an arrangement as shown in FIGS. 20a and 20b can be considered a fourth comparative example. At least one of the two stop means 300, 500 here moves on a non-circular closed path U1, as can be realized, for example, by a traction chain or toothed belt, or in general by a positively drivable closed belt or traction means. Such a traction means can advantageously be at least partially folded and/or reversed and/or located in a magazine in order to save space.

Representatives of an arrangement as shown in FIGS. 21a and 21b can be considered a fifth comparative example. The stop means 300, 500 in this case move at the same speed, operatively connected positively to one another, on circular paths U1, U2 of different sizes, the axis of the smaller circle U1 lying outside the larger circle U2.

Representatives of an arrangement as shown in FIGS. 22a and 22b can be considered a sixth comparative example. The stop means 300, 500 here move with different speeds, operatively connected positively via a transmitting gear unit, on two equal-sized or different-sized closed paths U1, U2, as can be realized for example by traction chains or toothed belts or generally by positively drivable closed belts or traction means. Such traction means can advantageously be at least partially folded and/or reversed and/or located in a magazine in order to save space.

Representatives of an arrangement as shown in FIGS. 23a and 23b can be considered a seventh comparative example. In this case, the stop means 300, 500 move on rotatable guide means with different speeds operatively connected positively via a transmitting gear unit; shown only schematically in the figure, on two equal-sized or different-sized circular paths U1, U2, the axis of the one circle U1 lying outside the axis of the other circle U2. Embodiments according to the present disclosure are presented below FIG. 24 presents an administration device comprising the alternative limiting mechanism according to the present disclosure in a state before use, e.g., the cartridge 3 is full and the piston rod 8 is in the most proximal position. The central axis of the pen defines a first longitudinal axis 72, which is the central axis for the dosing sleeve 50, housing 5, threaded sleeve 9, coupling sleeve 40 and the piston rod 8. The functioning of the dose setting is analogous to the comparative examples described above (and shown in FIGS. 1-23). The dosing sleeve 50 is threadedly engaged with a threaded sleeve 9. The threaded sleeve 9 is rotationally and axially fixed with respect to housing 5. The stop wheel 30 is inserted into clutch 40 and is in a non-tilted (horizontal or parallel to axis 72) position. During dose setting the user grasps and rotates rotary knob 11a and the dosing sleeve 50 is moved in the proximal direction due the threaded engagement with the threaded sleeve 9. The stop wheel 30 is rotated versus the non-rotating clutch 40 due to the engagement of the teeth 51 inside the outer wall of the dosing sleeve 50 and the teeth 31 of the stop wheel 30. During dose delivery the dosing sleeve 50 and the clutch 40 rotate together and the position of the stop wheel 30 relative to the clutch 40 or the dosing sleeve 50 is not changed. The position of cross sections through the driving zone A, stop zone B and limit stop zone C are indicated with a, b and c in FIG. 24. The cross sectional views of these zones A, B, C are shown in FIGS. 25a-c. In driving zone A the stop wheel 30 is engaged, with its external toothing 31 engaged with toothing 51 at the inside of the dosing sleeve 50. In the stop zone B, which is next to the driving zone A, the stop rib 32 of the stop wheel 30 can engage the teething 51 of the dosing sleeve 50. In the limit stop zone C, there is no engagement between the stop wheel 30 and the clutch 40 or the dosing sleeve 50 in the state of the pen before use. The structural arrangement of the parts is identical to the comparative prior art examples described above, the specific structural differences for the clutch 40, stop wheel 30 and the functioning are described in the following.

The clutch 40 has the cutout 41 for receiving the stop wheel 30 (FIG. 26). The proximal bearing 42 is analogous to the comparative examples above. Opposite to the proximal bearing there is a guidance 46 for guiding the distal shaft end 35 of the stop wheel 30. The guidance 46 is a recess that is preferably linear and oriented perpendicular to the longitudinal axis of the clutch 40. The clutch 40 has the limit stop 44 which comprises a complementary second sloped or curved surface 47 and a complementary fourth curved or sloped surface 48. Optionally, the recess 46 is not linear or may comprise holding means preventing the return of the stop from the tilted position to the non-tilted position.

The stop wheel 30 has the driving toothing 31 in zone A; the stop rib 32 in zone B and a first sloped or curved surface 60 and a third sloped or curved surface 61 in zone C, see FIGS. 27a-c. The outer cylindrical surface 63 having the external toothings 31, 32 is connected to the shaft of the stop wheel using support 62. The support is presented in the current example as a bridge formed between the shaft end 35 and the external surface 63; alternatively the stop wheel is a monolithic body or there are more than one bridges or spokes present to support the shaft. The objective is to provide a rigid, non-flexible connection between the outer surface 63 and the shaft ends 34, 35 of the stop wheel 30. In FIGS. 27a-c, the proximal and distal shaft ends (34, 35) are shown which define the second longitudinal axis 73 of the stop wheel 30.

The assembly of the stop wheel 30 and the clutch 40 is presented in FIG. 28 with the stop wheel 30 in the non-tilted position, e.g., the first longitudinal axis 72 and the second longitudinal axis 73 are oriented parallel to another. The proximal shaft end 34 is in abutment with proximal bearing 42 of the clutch 40, whereas the distal shaft end 35 is engaged with the guidance 46. When the stop wheel 30 tilts with respect to the clutch 40, the distal shaft end 35 moves through the guidance 46 and the tilting angle is restricted by abutment surface 49 at the end of the guidance 46.

After repeated dose setting and delivery, the piston rod 8 with flange 4 will have advanced the plug in the cartridge 3 towards the distal end of the cartridge 3. The setting of the last dose is restricted by the limiting mechanism to the amount of medication that is left in the cartridge. The stop wheel 30 has been tilted and blocks further dose setting in dial up (or dosing up) direction 70 (see arrow 70 in FIGS. 30a, 30c), whereas the last dose still can be corrected or dispensed. This situation is presented in FIG. 29, with the cross sections through the drive zone A, stop zone B and limit stop zone C in FIGS. 30a-c. In the drive zone A the toothed engagement (31, 51) between the dosing sleeve 50 and the stop wheel 30 ensures that rotation or torque is transmitted from the dosing sleeve 50 to the stop wheel 30. In the stop last dose position, the stop rib 32 of the stop wheel 30 abuts the stop wedge 52 of the dosing sleeve 50 in zone B and therefore the stop wheel 30 is tilted. As the stop wheel is tilted, the first sloped surface 60 of the stop wheel 30 engages the complementary second sloped surface 47 of the (non-rotating) clutch 40 forming a first gear guidance (60, 47). Rotation of the dosing sleeve 50 in the dial up direction (arrow 70) is transmitted to the stop wheel 30 in driving zone A and rotates the stop wheel 30 to bring the first gear guidance (60, 47) into engagement. The first gear guidance (60, 47) in zone C intends to slide the stop wheel 30 back to the non-tilted position, but this return movement is blocked by the abutment of the stop wedge 52 and the stop rib 32 in zone B. Because the return movement is blocked, torque in the dial up (or dosing up) direction 70 is transmitted from the dosing sleeve 50 to the stop wheel 30 and via the first gear guidance (60, 47) to the clutch 40. The clutch 40 is directly or indirectly coupled to the housing 5 via a one-way ratchet or clutch, which prevents rotation of the clutch 40 in the dial up direction 70. As a consequence, the dosing sleeve 50 cannot be rotated further in the dial up direction. During any dial down of the dosing sleeve 50, the stop wheel 30 is returned to the non-tilted position via a second gear guidance, explained next.

In the stop last dose position (FIG. 29) or when the stop wheel 30 is accidentally moved into the tilted position, for example due to an impact while dropping the administration device on the floor, a second gear guidance system ensures that the stop wheel 30 is returned to the non-tilted position, thereby improving the reliability of the dosing device. In FIG. 31, the administration device is shown with a full cartridge 3 and the piston rod 8 is in the most proximal position; dosing sleeve 50 has been dialed up to prepare a dose for injection. Nevertheless the stop wheel is (may become) accidentally tilted during the dose setting operation. As seen in FIGS. 32a-c, in drive zone A, the stop wheel 30 is (may be) driven by the engagement (31, 51) in the dial down (or dosing down) rotation direction (arrow 71). As a result, a second gear guidance (61, 48) is formed in limit stop zone C between the third sloped or curved surface 61 of the stop wheel 30 and the complementary fourth curved or sloped surface 48 of the clutch 40. In the current example, the third surface 61 is curve shaped whereas the fourth surface 48 is a surface with a linear slope. Other combinations between sloped-sloped, sloped-curved or curved-curved surfaces can be implemented. Upon further rotation of the dosing sleeve 50 in the dial down direction 71, the stop wheel 30 is tilted back (FIG. 33), because the stop wheel 30 is driven in drive zone A (FIGS. 34a-c) and also rotates in the dial down direction (arrow 71). The second gear guidance (61, 48) in zone C ensures that that stop wheel 30 is pushed back to the non-tilted position (FIG. 34c). The stop wheel 30 has been returned to the non-tilted position (FIG. 35) upon further rotation in the dial down direction, due to the engagement of the surfaces (61, 48) of the second gear guidance (FIGS. 36a-c).

The return movement of the stop wheel 30 by the second gear guidance (61, 48) occurs during dial down (dosing down) when the stop wheel has been forced in the tilted position when setting the last dose that equals the amount of medicament left in the cartridge, or the stop wheel is also returned during dose setting when the stop wheel is accidentally shifted to the tilted position during setting of a dose that does not equal the amount of medicament left in the cartridge.

Return of the stop wheel 30 to the non-tilted position during dial-up dosing movement of the stop wheel is explained in FIGS. 37a-c, 38a-c to 39a-c, when the stop wheel accidentally is shifted to the tilted position, e.g., not shifted during setting of the last dose as shown in FIGS. 29 and 30a-c where the stop wheel is forced to move into the tilted position in stop zone B (FIG. 30b). Upon rotation of the dose sleeve 50 in the dial up rotation direction 70, the stop wheel 30 is driven in the same rotation direction by the toothed engagement (31, 51) in drive zone A (FIG. 37a). When the stop wheel is not in the stop last dose position, the stop rib 32 can engage the teething 51 in stop zone B, because the stop wheel has not been rotated through the full period that equals the amount of medication in a full cartridge, e.g., in this situation the stop rib 32 does not engage the wedge 52 as shown in FIG. 30b, zone B. As the stop wheel 30 rotates for dial up, the first sloped or curved surface 60 of the stop wheel 30 engages the complementary second curved or sloped surface 47 of the (non-rotating) clutch 40 to form the first gear guidance (60, 47) (FIG. 37c, Zone C). Upon further rotation of the dosing sleeve 50 in the dial up direction 70, the stop wheel 30 rotates with respect to the non-rotating clutch 40, and the first gear guidance (60, 47) in zone C shifts the stop wheel back to the non-tilted position (FIGS. 38c and 39c, zone C). Because the stop rib 32 in zone B can engage the toothing 51 of the dosing sleeve 50, the shifting back is not hindered and also dial up of the dosing sleeve is not hindered.

The materials, surfaces and geometry (slopes) are optimized and selected to fine-tune the frictional interaction of the gear guidances (i.e., first gear guidance (60, 47); second gear guidance (61, 48)) to prevent self-locking, or blocking engagement during dose setting and obtain an effective blocking in the stop last dose position.

LIST OF REFERENCE NUMBERS

1 Protective cap
2 Cartridge holder
2a Needle holder
3 Cartridge
4 Flange
5 Housing
6 Housing insert
7 Threaded nut
8 Threaded rod
8a End of thread
8g Thread
9 Threaded sleeve
11 a Rotary knob
13 Dosing click spring
14 Ejection knob
30 Stop wheel, second limiting means
31 Drive toothing
32 Stop rib, second stop or stop means
33 Counter-limit stop, second limit stop or stop means
34 Proximal shaft end
35 Distal shaft end 36 Rotational shaft
37 Spoke means
38 Slider in transverse guide
39 Spring means
300 Second stop or stop means
40 Coupling, coupling sleeve
41 Cutout
42 Proximal bearing
43 Distal bearing
44 Limit stop, first limit stop or stop means
45 Gear cam
46 Guidance for distal shaft end
47 Complementary second sloped or curved surface
48 Complementary fourth sloped or curved surface
49 Abutment surface
50 Dosing sleeve, first limiting means
50a Outer wall
51 Toothing (inner wall)
52 Stop wedge, first stop or stop means
60 First sloped or curved surface
61 Third sloped or curved surface
62 Support shaft
63 Outer surface
70 Dial up direction
71 Dial down direction
72 First longitudinal axis
73 Second longitudinal axis
500 First stop or stop means
U1 First path curve, circular path
U2 Second path curve, circular path
a cross section drive zone A
b cross section stop zone B
c cross section limit stop zone C
(60, 47) First gear guidance
(61, 48) Second gear guidance
(31, 51) Toothed engagement

The invention claimed is:

1. A dosing device with a dose limiting mechanism for an administration device, comprising:
a sleeve-like dosing member defining a first longitudinal axis, comprising an inner wall with a toothing and a first stop, and an outer wall,
a coupling sleeve coaxially arranged within the dosing member which is configured to be rotatable relative to the dosing member during dosing movements of the dosing member and being rotationally coupled to the dosing member during dose delivery movements,
a stop wheel defining a second longitudinal axis, comprising a toothing on an outside that meshes with the toothing of the dosing member, and a second stop,
the stop wheel being rotatably received in the coupling sleeve by at least one bearing point in the coupling sleeve such that the stop wheel is movable from a first position wherein the first and second longitudinal axis are arranged parallel to one another to a second position whereby the second longitudinal axis is tilted with respect to the first longitudinal axis,
wherein during dosing movements, the dosing member is rotated in a first direction with respect to the coupling sleeve for dial up, and in a second rotation direction which is opposite to the first rotation direction for dial down, and the stop wheel follows the dosing movements of the dosing member with a defined transmission ratio, and wherein the first stop and second stop each describes by movement a path curve that is closed and can be run through one or multiple times until the two path curves come so close together that the first stop and second stop contact one another in a stop position,
wherein during dose delivery movements, the stop wheel does not move relative to the dosing member, and wherein the dosing device further comprises:
a first gear guidance arranged between the coupling sleeve and the stop wheel which is configured to move the stop wheel from the second position back to the first position during dial up when the first stop and the second stop are not in the stop position, and
a second gear guidance arranged between the coupling sleeve and the stop wheel which is configured to move the stop wheel from the second position back to the first position during dial down, wherein the stop wheel is moved from the first to the second position when the first stop and second stop contact one another in the stop position thereby preventing the first gear guidance from moving the stop wheel back to the first position and blocking dial up dosing movements.

2. The dosing device according to claim 1 wherein the toothing on the dosing member inner wall comprises teeth and tooth interstices and the first stop is formed as a wedge that fills out at least a part of a tooth interstice.

3. The dosing device according to claim 1 wherein the second stop is formed as a rib on the outside of the stop wheel.

4. The dosing device according to claim 3 wherein the rib is an extended tooth of the toothing on the outside of the stop wheel.

5. The dosing device according to claim 1 wherein the coupling sleeve is rotationally couplable to a housing via a one-way ratchet.

6. The dosing device according to claim 1 wherein the stop wheel comprises two shaft ends arranged along the second longitudinal axis, one of the two shaft ends is rotatably received in a bearing located at the center of the coupling sleeve, whereas the other shaft end of the two shaft ends is axially guided by the coupling sleeve in a direction perpendicular to the second longitudinal axis.

7. The dosing device according to claim 1, wherein the dosing member surrounds the stop wheel at least in part, or is adjacent thereto.

8. The dosing device according to claim 1, wherein the second longitudinal axis is parallel and offset to the first longitudinal axis of the dosing member when the stop wheel is in the first position.

9. The dosing device according to claim 1 wherein the stop wheel has an outer surface that is axially subdivided along the second longitudinal axis into at least three regions, wherein the toothing on the outside of the stop wheel is located in a first region of the at least three regions, and the second stop is located in a region adjacent to the first region, and the first and second gear guidances; are located in a third region that is adjacent to the second region.

10. The dosing device according to claim 1 wherein the first gear guidance is formed by a first sloped or curved surface on the stop wheel and a complementary second sloped or curved surface on the coupling sleeve, wherein during dial up movement of the dosing member the first curved or sloped surface on the stop wheel abuts and may slide along the second curved or sloped surface of the coupling sleeve when the stop wheel is in the second position, or in an intermediate position between the first position and the second position.

11. The dosing device according to claim 1, wherein the second gear guidance is formed by a third sloped or curved surface on the stop wheel and a complementary fourth sloped or curved surface on the coupling sleeve, wherein during dial down movement of the dosing member the third curved or sloped surface on the stop wheel abuts and slides along the fourth curved or sloped surface of the coupling sleeve when the stop wheel is in the second position, or in an intermediate position between the first position and the second position.

12. The dosing device according to claim 1 wherein the first stop moves on a circular path curve and whereby the stop wheel is axially arranged in such a manner that its toothing on the outside meshes with the toothing on the inner wall of the dosing member and the second stop moves on its path curve due to relative movement between the dosing member and the coupling sleeve during dosing movements.

13. An injection device comprising the dosing device according to claim 1 for setting a product dosage to be administered and for displaying a set product dosage, the injection device further comprising a cartridge for a product, a cartridge holder for attaching the cartridge to the dosing device, a conveying device for conveying the product, the conveying device comprising a piston rod, which is moveable in a conveyance direction in order to eject the set product dosage from the cartridge in a conveyance stroke corresponding to the set product dosage.

14. The injection device according to claim 13, wherein the coupling sleeve can operatively connect the dosing device to the conveying device, wherein the coupling sleeve is configured such that the product dosage to be administered can be set independently from the conveying device, and the coupling sleeve is configured such that the dosing device can be operatively coupled to the conveying device during administration of the product dosage.

15. An injection device according to claim 13, wherein setting of a dose beyond an amount of product left in the cartridge is prevented when the first stop and second stop contact one another at the stop position thereby moving the stop wheel from the first to the second position and preventing the first gear guidance from moving the stop wheel back to the first position and thereby blocking dial up dose setting movements.

16. A dosing device with a dose limiting mechanism for an administration device, the dose limiting mechanism comprising:
- a sleeve-like dosing member defining a first longitudinal axis, the sleeve-like dosing member comprising an inner wall with a toothing and a first stop;
- a coupling sleeve coaxially arranged within the dosing member which is configured to be rotatable relative to the dosing member during dosing movements of the dosing member and being rotationally coupled to the dosing member during dose delivery movements,
- a stop wheel defining a second longitudinal axis, the stop wheel comprising a toothing configured to mesh with the toothing of the dosing member and a second stop;
- a first gear guidance formed by a first sloped or curved surface of the stop wheel and a complementary second sloped or curved surface of the coupling sleeve; and
- a second gear guidance formed by a third sloped or curved surface of the stop wheel and a complementary fourth sloped or curved surface of the coupling sleeve,
- wherein the stop wheel is rotatably received in the coupling sleeve by at least one bearing point in the coupling sleeve such that the stop wheel is movable from a first position in which the first longitudinal axis and the second longitudinal axis are arranged parallel to one another, to a second position in which the second longitudinal axis is tilted with respect to the first longitudinal axis,
- wherein during dosing movements, the dosing member is rotated in a first direction with respect to the coupling sleeve for dosing up, and in a second rotation direction which is opposite to the first rotation direction for dosing down, and the stop wheel follows the dosing movements of the dosing member with a defined transmission ratio,
- wherein dosing movements of the first stop and the second stop each define a respective path curve so that the path curve of the first stop and the path curve of the second stop come so close together that the first stop and second stop contact one another in a stop position,
- wherein during dose delivery movements, the stop wheel does not move relative to the dosing member,
- wherein during dosing up movements of the dosing member, the first curved or sloped surface of the stop wheel abuts and slides along the second curved or sloped surface of the coupling sleeve when the stop wheel is in the second position, or out of the first position, such that the first gear guidance is configured to move the stop wheel from the second position back to the first position when the first stop and the second stop are not in the stop position, and
- wherein during dosing down movements of the dosing member, the third curved or sloped surface of the stop wheel abuts and slides along the fourth curved or sloped surface of the coupling sleeve when the stop wheel is in the second position, or out of the first position, such that the second gear guidance is configured to move the stop wheel from the second position back to the first position, and
- wherein the stop wheel is moved from the first position to the second position when the first and second stop contact one another in the stop position thereby preventing the first gear guidance from moving the stop wheel back to the first position and blocking dosing up dosing movements.

17. The dosing device according to claim 16, wherein each respective path curve is closed and can be run through one or multiple times until the path curve of the first stop and the path curve of the second stop come so close together that the first stop and second stop contact one another in the stop position.

18. The dosing device according to claim 16 wherein the stop wheel has its toothing in a zone A; the second stop is a rib in a zone B of the stop wheel adjacent to zone A, and each of the first and second gear guidances is configured in a zone C of the stop wheel adjacent zone B and spaced from zone A by zone B, whereby if the stop wheel comes accidently into the second, tilted position, but the first stop and second stop are not in a stop position, and the stop wheel is rotated for dosing dial up, the respective sloped or curved surface of the stop wheel and complementary sloped or curved surface of the coupling sleeve first gear guidance come into abutment in zone C during the dosing dial up and the stop wheel will be pushed back to a non-tilted position.

* * * * *